United States Patent
Bays et al.

(10) Patent No.: US 11,771,443 B2
(45) Date of Patent: *Oct. 3, 2023

(54) JOINT SPACER SYSTEMS AND METHODS

(71) Applicant: Treace Medical Concepts, Inc., Ponte Vedra, FL (US)

(72) Inventors: F. Barry Bays, Collierville, TN (US); Paul Dayton, Ankeny, IA (US); Joe William Ferguson, Ponte Vedra Beach, FL (US); Carlos Eduardo Gil, Memphis, TN (US); Robert D. Santrock, Morgantown, WV (US); Sean F. Scanlan, Jacksonville, FL (US); W. Bret Smith, Lexington, SC (US); John T. Treace, Ponte Vedra Beach, FL (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/057,762

(22) Filed: Nov. 21, 2022

(65) Prior Publication Data

US 2023/0090511 A1    Mar. 23, 2023

Related U.S. Application Data

(63) Continuation of application No. 16/750,829, filed on Jan. 23, 2020, which is a continuation of application
(Continued)

(51) Int. Cl.
*A61B 17/17* (2006.01)
*A61B 17/15* (2006.01)
(Continued)

(52) U.S. Cl.
CPC .......... *A61B 17/1775* (2016.11); *A61B 17/15* (2013.01); *A61B 17/151* (2013.01);
(Continued)

(58) Field of Classification Search
CPC ............ A61B 17/1682; A61B 17/8061; A61B 17/1764
See application file for complete search history.

(56) References Cited

U.S. PATENT DOCUMENTS

| 3,664,022 A | 5/1972 | Small |
| 4,069,824 A | 1/1978 | Weinstock |

(Continued)

FOREIGN PATENT DOCUMENTS

| AU | 2009227957 B2 | 7/2014 |
| CA | 2491824 A1 | 9/2005 |

(Continued)

OTHER PUBLICATIONS

Rx-Fix Mini Rail External Fixator, Wright Medical Technology, Brochure, Aug. 15, 2014, 2 pages.
(Continued)

*Primary Examiner* — Andrew Yang
(74) *Attorney, Agent, or Firm* — Fredrikson & Byron, P.A.

(57) ABSTRACT

A method of preparing a tarsometatarsal joint can include imaging a tarsometatarsal joint of a patient between a metatarsal and a cuneiform to determine a size and/or angle of a wedge-shaped bone portion to be cut at the tarsometatarsal joint. The method can include obtaining a bone preparation guide that includes a first guide surface positionable over the metatarsal and a second guide surface positionable over the cuneiform, where an angle of the first guide surface relative to the second guide surface is selected corresponding to the size and/or angle of the wedge-shaped
(Continued)

bone portion to be cut as determined via imaging of the tarsometatarsal joint. The method can include positioning the guide surfaces over the metatarsal and cuneiform and guiding a tissue removing instrument with the guide surfaces to cut an end of the metatarsal and to cut an end of the cuneiform.

30 Claims, 18 Drawing Sheets

Related U.S. Application Data

No. 15/267,531, filed on Sep. 16, 2016, now Pat. No. 10,575,862.

(60) Provisional application No. 62/366,219, filed on Jul. 25, 2016, provisional application No. 62/220,530, filed on Sep. 18, 2015.

(51) Int. Cl.
*A61B 17/56* (2006.01)
*A61B 17/16* (2006.01)
*A61B 17/80* (2006.01)
*A61B 17/88* (2006.01)
*A61B 17/02* (2006.01)

(52) U.S. Cl.
CPC ........ *A61B 17/152* (2013.01); *A61B 17/1682* (2013.01); *A61B 17/1739* (2013.01); *A61B 17/562* (2013.01); *A61B 17/8061* (2013.01); *A61B 17/8866* (2013.01); *A61B 17/025* (2013.01); *A61B 17/1728* (2013.01); *A61B 2017/564* (2013.01); *A61B 2017/565* (2013.01)

(56) References Cited

U.S. PATENT DOCUMENTS

| | | |
|---|---|---|
| 4,159,716 A | 7/1979 | Borchers |
| 4,187,840 A | 2/1980 | Watanabe |
| 4,335,715 A | 6/1982 | Kirkley |
| 4,338,927 A | 7/1982 | Volkov et al. |
| 4,349,018 A | 9/1982 | Chambers |
| 4,409,973 A | 10/1983 | Neufeld |
| 4,440,168 A | 4/1984 | Warren |
| 4,501,268 A | 2/1985 | Comparetto |
| 4,502,474 A | 3/1985 | Comparetto |
| 4,509,511 A | 4/1985 | Neufeld |
| 4,565,191 A | 1/1986 | Slocum |
| 4,570,624 A | 2/1986 | Wu |
| 4,627,425 A | 12/1986 | Reese |
| 4,628,919 A | 12/1986 | Clyburn |
| 4,632,102 A | 12/1986 | Comparetto |
| 4,664,102 A | 5/1987 | Comparetto |
| 4,708,133 A | 11/1987 | Comparetto |
| 4,736,737 A | 4/1988 | Fargie et al. |
| 4,750,481 A | 6/1988 | Reese |
| 4,754,746 A | 7/1988 | Cox |
| 4,757,810 A | 7/1988 | Reese |
| 4,895,141 A | 1/1990 | Koeneman et al. |
| 4,952,214 A | 8/1990 | Comparetto |
| 4,959,066 A | 9/1990 | Dunn et al. |
| 4,978,347 A | 12/1990 | Ilizarov |
| 4,988,349 A | 1/1991 | Pennig |
| 4,995,875 A | 2/1991 | Coes |
| 5,021,056 A | 6/1991 | Hofmann et al. |
| 5,035,698 A | 7/1991 | Comparetto |
| 5,042,983 A | 8/1991 | Rayhack |
| 5,049,149 A | 9/1991 | Schmidt |
| 5,053,039 A | 10/1991 | Hofmann et al. |
| 5,078,719 A | 1/1992 | Schreiber |
| 5,112,334 A | 5/1992 | Alchermes et al. |
| 5,147,364 A | 9/1992 | Comparetto |
| 5,176,685 A | 1/1993 | Rayhack |
| 5,207,676 A | 5/1993 | Canadell et al. |
| 5,246,444 A | 9/1993 | Schreiber |
| 5,254,119 A | 10/1993 | Schreiber |
| 5,312,412 A | 5/1994 | Whipple |
| 5,358,504 A | 10/1994 | Paley et al. |
| 5,364,402 A | 11/1994 | Mumme et al. |
| 5,374,271 A | 12/1994 | Hwang |
| 5,413,579 A | 5/1995 | Du Toit |
| 5,417,694 A | 5/1995 | Marik et al. |
| 5,449,360 A | 9/1995 | Schreiber |
| 5,470,335 A | 11/1995 | Du Toit |
| 5,490,854 A | 2/1996 | Fisher et al. |
| 5,529,075 A | 6/1996 | Clark |
| 5,540,695 A | 7/1996 | Levy |
| 5,578,038 A | 11/1996 | Slocum |
| 5,586,564 A | 12/1996 | Barre, I et al. |
| 5,601,565 A | 2/1997 | Huebner |
| 5,613,969 A | 3/1997 | Jenkins, Jr. |
| 5,620,442 A | 4/1997 | Bailey et al. |
| 5,620,448 A | 4/1997 | Puddu |
| 5,643,270 A | 7/1997 | Combs |
| 5,667,510 A | 9/1997 | Combs |
| H1706 H | 1/1998 | Mason |
| 5,722,978 A | 3/1998 | Jenkins |
| 5,749,875 A | 5/1998 | Puddu |
| 5,779,709 A | 7/1998 | Harris et al. |
| 5,788,695 A | 8/1998 | Richardson |
| 5,803,924 A | 9/1998 | Oni et al. |
| 5,810,822 A | 9/1998 | Mortier |
| 5,843,085 A | 12/1998 | Graser |
| 5,893,553 A | 4/1999 | Pinkous |
| 5,911,724 A | 6/1999 | Wehrli |
| 5,935,128 A | 8/1999 | Carter et al. |
| 5,941,877 A | 8/1999 | Viegas et al. |
| 5,951,556 A | 9/1999 | Faccioli et al. |
| 5,980,526 A | 11/1999 | Johnson et al. |
| 5,984,931 A | 11/1999 | Greenfield |
| 6,007,535 A | 12/1999 | Rayhack et al. |
| 6,027,504 A | 2/2000 | McGuire |
| 6,030,391 A | 2/2000 | Brainard et al. |
| 6,162,223 A | 12/2000 | Orsak et al. |
| 6,171,309 B1 | 1/2001 | Huebner |
| 6,203,545 B1 | 3/2001 | Stoffella |
| 6,248,109 B1 | 6/2001 | Stoffella |
| 6,391,031 B1 | 5/2002 | Toomey |
| 6,478,799 B1 | 11/2002 | Williamson |
| 6,511,481 B2 | 1/2003 | von Hoffmann et al. |
| 6,547,793 B1 | 4/2003 | McGuire |
| 6,676,662 B1 | 1/2004 | Bagga et al. |
| 6,719,773 B1 | 4/2004 | Boucher et al. |
| 6,743,233 B1 | 6/2004 | Baldwin et al. |
| 6,755,838 B2 | 6/2004 | Trnka |
| 6,796,986 B2 | 9/2004 | Duffner |
| 6,859,661 B2 | 2/2005 | Tuke |
| 7,018,383 B2 | 3/2006 | McGuire |
| 7,033,361 B2 | 4/2006 | Collazo |
| 7,097,647 B2 | 8/2006 | Segler et al. |
| 7,112,204 B2 | 9/2006 | Justin et al. |
| 7,153,310 B2 | 12/2006 | Ralph et al. |
| 7,182,766 B1 | 2/2007 | Mogul |
| 7,241,298 B2 | 7/2007 | Nemec et al. |
| 7,282,054 B2 | 10/2007 | Steffensmeier et al. |
| 7,377,924 B2 | 5/2008 | Raistrick et al. |
| 7,465,303 B2 | 12/2008 | Riccione et al. |
| 7,540,874 B2 | 6/2009 | Trumble et al. |
| 7,572,258 B2 | 8/2009 | Stiernborg |
| 7,641,660 B2 | 1/2010 | Lakin et al. |
| D610,257 S | 2/2010 | Horton |
| 7,686,811 B2 | 3/2010 | Byrd et al. |
| 7,691,108 B2 | 4/2010 | Lavallee |
| 7,763,026 B2 | 7/2010 | Egger et al. |
| D629,900 S | 12/2010 | Fisher |
| 7,967,823 B2 | 6/2011 | Ammann et al. |
| 7,972,338 B2 | 7/2011 | O'Brien |
| D646,389 S | 10/2011 | Claypool et al. |
| 8,057,478 B2 | 11/2011 | Kuczynski et al. |
| 8,062,301 B2 | 11/2011 | Ammann et al. |
| D651,315 S | 12/2011 | Bertoni et al. |

(56) References Cited

U.S. PATENT DOCUMENTS

| | | |
|---|---|---|
| D651,316 S | 12/2011 | May et al. |
| 8,080,010 B2 | 12/2011 | Schulz et al. |
| 8,080,045 B2 | 12/2011 | Wotton, III |
| 8,083,746 B2 | 12/2011 | Novak |
| 8,123,753 B2 | 2/2012 | Poncet |
| 8,137,406 B2 | 3/2012 | Novak et al. |
| 8,147,530 B2 | 4/2012 | Strnad et al. |
| 8,167,918 B2 | 5/2012 | Strnad et al. |
| 8,172,848 B2 | 5/2012 | Tomko et al. |
| 8,192,441 B2 | 6/2012 | Collazo |
| 8,197,487 B2 | 6/2012 | Poncet et al. |
| 8,231,623 B1 | 7/2012 | Jordan |
| 8,231,663 B2 | 7/2012 | Kay et al. |
| 8,236,000 B2 | 8/2012 | Ammann et al. |
| 8,246,561 B1 | 8/2012 | Agee et al. |
| D666,721 S | 9/2012 | Wright et al. |
| 8,262,664 B2 | 9/2012 | Justin et al. |
| 8,277,459 B2 | 10/2012 | Sand et al. |
| 8,282,644 B2 | 10/2012 | Edwards |
| 8,282,645 B2 | 10/2012 | Lawrence et al. |
| 8,292,966 B2 | 10/2012 | Morton |
| 8,303,596 B2 | 11/2012 | Plassky et al. |
| 8,313,492 B2 | 11/2012 | Wong et al. |
| 8,323,289 B2 | 12/2012 | Re |
| 8,337,503 B2 | 12/2012 | Lian |
| 8,343,159 B2 | 1/2013 | Bennett |
| 8,377,105 B2 | 2/2013 | Buescher |
| D679,395 S | 4/2013 | Wright et al. |
| 8,409,209 B2 | 4/2013 | Ammann et al. |
| 8,435,246 B2 | 5/2013 | Fisher et al. |
| 8,475,462 B2 | 7/2013 | Thomas et al. |
| 8,496,662 B2 | 7/2013 | Novak et al. |
| 8,523,870 B2 | 9/2013 | Green, II et al. |
| 8,529,571 B2 | 9/2013 | Horan et al. |
| 8,540,777 B2 | 9/2013 | Ammann et al. |
| 8,545,508 B2 | 10/2013 | Collazo |
| D694,884 S | 12/2013 | Mooradian et al. |
| D695,402 S | 12/2013 | Dacosta et al. |
| 8,652,142 B2 | 2/2014 | Geissler |
| 8,657,820 B2 | 2/2014 | Kubiak et al. |
| D701,303 S | 3/2014 | Cook |
| 8,672,945 B2 | 3/2014 | Lavallee et al. |
| 8,696,716 B2 | 4/2014 | Kartalian et al. |
| 8,702,715 B2 | 4/2014 | Ammann et al. |
| D705,929 S | 5/2014 | Frey |
| 8,715,363 B2 | 5/2014 | Ratron et al. |
| 8,728,084 B2 | 5/2014 | Berelsman et al. |
| 8,758,354 B2 | 6/2014 | Habegger et al. |
| 8,764,760 B2 | 7/2014 | Metzger et al. |
| 8,764,763 B2 | 7/2014 | Wong et al. |
| 8,771,279 B2 | 7/2014 | Philippon et al. |
| 8,777,948 B2 | 7/2014 | Bernsteiner |
| 8,784,427 B2 | 7/2014 | Fallin et al. |
| 8,784,457 B2 | 7/2014 | Graham |
| 8,795,286 B2 | 8/2014 | Sand et al. |
| 8,801,727 B2 | 8/2014 | Chan et al. |
| 8,808,303 B2 | 8/2014 | Stemniski et al. |
| 8,828,012 B2 | 9/2014 | May et al. |
| 8,858,602 B2 | 10/2014 | Weiner et al. |
| 8,882,778 B2 | 11/2014 | Ranft |
| 8,882,816 B2 | 11/2014 | Kartalian et al. |
| 8,888,785 B2 | 11/2014 | Ammann et al. |
| D720,456 S | 12/2014 | Dacosta et al. |
| 8,900,247 B2 | 12/2014 | Tseng et al. |
| 8,906,026 B2 | 12/2014 | Ammann et al. |
| 8,945,132 B2 | 2/2015 | Plassky et al. |
| 8,998,903 B2 | 4/2015 | Price et al. |
| 8,998,904 B2 | 4/2015 | Zeetser et al. |
| 9,023,052 B2 | 5/2015 | Lietz et al. |
| 9,044,250 B2 | 6/2015 | Olsen et al. |
| 9,060,822 B2 | 6/2015 | Lewis et al. |
| 9,089,376 B2 | 7/2015 | Medoff et al. |
| 9,101,421 B2 | 8/2015 | Blacklidge |
| 9,107,715 B2 | 8/2015 | Blitz et al. |
| 9,113,920 B2 | 8/2015 | Ammann et al. |
| D740,424 S | 10/2015 | Dacosta et al. |
| D765,844 S | 9/2016 | DaCosta |
| D766,434 S | 9/2016 | DaCosta |
| D766,437 S | 9/2016 | DaCosta |
| D766,438 S | 9/2016 | DaCosta |
| D766,439 S | 9/2016 | DaCosta |
| 9,452,057 B2 | 9/2016 | Dacosta et al. |
| 9,522,023 B2 | 12/2016 | Haddad et al. |
| 9,750,538 B2 | 9/2017 | Soffiatti et al. |
| 9,785,747 B2 | 10/2017 | Geebelen |
| 9,980,760 B2 | 5/2018 | Dacosta et al. |
| 10,028,750 B2 | 7/2018 | Rose |
| 10,064,631 B2 | 9/2018 | Dacosta et al. |
| 10,159,499 B2 | 12/2018 | Dacosta et al. |
| 10,292,713 B2 | 5/2019 | Fallin et al. |
| 10,327,829 B2 | 6/2019 | Dacosta et al. |
| 10,376,268 B2 | 8/2019 | Fallin et al. |
| 10,470,779 B2 | 11/2019 | Fallin et al. |
| 10,779,867 B2 | 9/2020 | Penzimer et al. |
| 11,304,705 B2 | 4/2022 | Fallin et al. |
| 2002/0099381 A1 | 7/2002 | Maroney |
| 2002/0107519 A1 | 8/2002 | Dixon et al. |
| 2002/0165552 A1 | 11/2002 | Duffner |
| 2002/0198531 A1 | 12/2002 | Millard et al. |
| 2004/0010259 A1 | 1/2004 | Keller et al. |
| 2004/0039394 A1 | 2/2004 | Conti et al. |
| 2004/0097946 A1 | 5/2004 | Dietzel et al. |
| 2004/0138669 A1 | 7/2004 | Horn |
| 2005/0004676 A1 | 1/2005 | Schon et al. |
| 2005/0059978 A1 | 3/2005 | Sherry et al. |
| 2005/0070909 A1 | 3/2005 | Egger et al. |
| 2005/0075641 A1 | 4/2005 | Singhatat et al. |
| 2005/0101961 A1 | 5/2005 | Huebner et al. |
| 2005/0149042 A1 | 7/2005 | Metzger |
| 2005/0228389 A1 | 10/2005 | Stiernborg |
| 2005/0251147 A1 | 11/2005 | Novak |
| 2005/0267482 A1 | 12/2005 | Hyde, Jr. |
| 2005/0273112 A1 | 12/2005 | McNamara |
| 2006/0129163 A1 | 6/2006 | McGuire |
| 2006/0206044 A1 | 9/2006 | Simon |
| 2006/0217733 A1 | 9/2006 | Plassky et al. |
| 2006/0229621 A1 | 10/2006 | Cadmus |
| 2006/0241607 A1 | 10/2006 | Myerson et al. |
| 2006/0241608 A1 | 10/2006 | Myerson et al. |
| 2006/0264961 A1 | 11/2006 | Murray-Brown |
| 2007/0010818 A1 | 1/2007 | Stone et al. |
| 2007/0123857 A1 | 5/2007 | Deffenbaugh et al. |
| 2007/0233138 A1 | 10/2007 | Figueroa et al. |
| 2007/0265634 A1 | 11/2007 | Weinstein |
| 2007/0276383 A1 | 11/2007 | Rayhack |
| 2008/0009863 A1 | 1/2008 | Bond et al. |
| 2008/0015603 A1 | 1/2008 | Collazo |
| 2008/0039850 A1 | 2/2008 | Rowley et al. |
| 2008/0091197 A1 | 4/2008 | Coughlin |
| 2008/0140081 A1 | 6/2008 | Heavener et al. |
| 2008/0147073 A1 | 6/2008 | Ammann et al. |
| 2008/0172054 A1 | 7/2008 | Claypool et al. |
| 2008/0195215 A1 | 8/2008 | Morton |
| 2008/0208252 A1 | 8/2008 | Holmes |
| 2008/0262500 A1 | 10/2008 | Collazo |
| 2008/0269908 A1 | 10/2008 | Warburton |
| 2008/0288004 A1 | 11/2008 | Schendel |
| 2009/0036893 A1 | 2/2009 | Kartalian et al. |
| 2009/0036931 A1 | 2/2009 | Pech et al. |
| 2009/0054899 A1 | 2/2009 | Ammann et al. |
| 2009/0093849 A1 | 4/2009 | Grabowski |
| 2009/0105767 A1 | 4/2009 | Reiley |
| 2009/0118733 A1 | 5/2009 | Orsak et al. |
| 2009/0198244 A1 | 8/2009 | Leibel |
| 2009/0198279 A1 | 8/2009 | Zhang et al. |
| 2009/0222047 A1 | 9/2009 | Graham |
| 2009/0254092 A1 | 10/2009 | Albiol |
| 2009/0254126 A1 | 10/2009 | Orbay et al. |
| 2009/0287309 A1 | 11/2009 | Walch et al. |
| 2010/0069910 A1 | 3/2010 | Hasselman |
| 2010/0121334 A1 | 5/2010 | Couture et al. |
| 2010/0130981 A1 | 5/2010 | Richards |
| 2010/0152782 A1 | 6/2010 | Stone et al. |
| 2010/0168799 A1 | 7/2010 | Schumer |

(56) References Cited

U.S. PATENT DOCUMENTS

| | | |
|---|---|---|
| 2010/0185245 A1 | 7/2010 | Paul et al. |
| 2010/0249779 A1 | 9/2010 | Hotchkiss et al. |
| 2010/0256687 A1 | 10/2010 | Neufeld et al. |
| 2010/0318088 A1 | 12/2010 | Warne et al. |
| 2010/0324556 A1 | 12/2010 | Tyber et al. |
| 2011/0009865 A1 | 1/2011 | Orfaly |
| 2011/0093084 A1 | 4/2011 | Morton |
| 2011/0118739 A1 | 5/2011 | Tyber et al. |
| 2011/0178524 A1 | 7/2011 | Lawrence et al. |
| 2011/0245835 A1 | 10/2011 | Dodds et al. |
| 2011/0288550 A1 | 11/2011 | Orbay et al. |
| 2011/0301648 A1 | 12/2011 | Lofthouse et al. |
| 2012/0016426 A1 | 1/2012 | Robinson |
| 2012/0065689 A1 | 3/2012 | Prasad et al. |
| 2012/0078258 A1 | 3/2012 | Lo et al. |
| 2012/0123420 A1 | 5/2012 | Honiball |
| 2012/0123484 A1 | 5/2012 | Lietz et al. |
| 2012/0130376 A1 | 5/2012 | Loring et al. |
| 2012/0130382 A1 | 5/2012 | Iannotti et al. |
| 2012/0130383 A1 | 5/2012 | Budoff |
| 2012/0184961 A1 | 7/2012 | Johannaber |
| 2012/0185056 A1 | 7/2012 | Warburton |
| 2012/0191199 A1 | 7/2012 | Raemisch |
| 2012/0239045 A1 | 9/2012 | Li |
| 2012/0253350 A1 | 10/2012 | Anthony et al. |
| 2012/0265301 A1 | 10/2012 | Demers et al. |
| 2012/0277745 A1 | 11/2012 | Lizee |
| 2012/0303033 A1 | 11/2012 | Weiner et al. |
| 2012/0330135 A1 | 12/2012 | Millahn et al. |
| 2013/0012949 A1 | 1/2013 | Fallin et al. |
| 2013/0035694 A1 | 2/2013 | Grimm et al. |
| 2013/0085499 A1 | 4/2013 | Lian |
| 2013/0085502 A1 | 4/2013 | Harrold |
| 2013/0096563 A1 | 4/2013 | Meade et al. |
| 2013/0131821 A1 | 5/2013 | Cachia |
| 2013/0150900 A1 | 6/2013 | Haddad et al. |
| 2013/0150903 A1 | 6/2013 | Vincent |
| 2013/0158556 A1 | 6/2013 | Jones et al. |
| 2013/0165936 A1 | 6/2013 | Myers |
| 2013/0165938 A1 | 6/2013 | Chow et al. |
| 2013/0172942 A1 | 7/2013 | Lewis et al. |
| 2013/0184714 A1 | 7/2013 | Kaneyama et al. |
| 2013/0190765 A1 | 7/2013 | Harris et al. |
| 2013/0190766 A1 | 7/2013 | Harris et al. |
| 2013/0204259 A1 | 8/2013 | Zajac |
| 2013/0226248 A1 | 8/2013 | Hatch et al. |
| 2013/0226252 A1 | 8/2013 | Mayer |
| 2013/0231668 A1 | 9/2013 | Olsen et al. |
| 2013/0237987 A1 | 9/2013 | Graham |
| 2013/0237989 A1 | 9/2013 | Bonutti |
| 2013/0267956 A1 | 10/2013 | Terrill et al. |
| 2013/0310836 A1 | 11/2013 | Raub et al. |
| 2013/0325019 A1 | 12/2013 | Thomas et al. |
| 2013/0325076 A1 | 12/2013 | Palmer et al. |
| 2013/0331845 A1 | 12/2013 | Horan et al. |
| 2013/0338785 A1 | 12/2013 | Wong |
| 2014/0005672 A1 | 1/2014 | Edwards et al. |
| 2014/0025127 A1 | 1/2014 | Richter |
| 2014/0039501 A1 | 2/2014 | Schickendantz et al. |
| 2014/0039561 A1 | 2/2014 | Weiner et al. |
| 2014/0046387 A1 | 2/2014 | Waizenegger |
| 2014/0074099 A1 | 3/2014 | Vigneron et al. |
| 2014/0074101 A1 | 3/2014 | Collazo |
| 2014/0094861 A1 | 4/2014 | Fallin |
| 2014/0094924 A1 | 4/2014 | Hacking et al. |
| 2014/0135775 A1 | 5/2014 | Maxson et al. |
| 2014/0163563 A1 | 6/2014 | Reynolds et al. |
| 2014/0171953 A1 | 6/2014 | Gonzalvez et al. |
| 2014/0180342 A1 | 6/2014 | Lowery et al. |
| 2014/0188139 A1 | 7/2014 | Fallin et al. |
| 2014/0194884 A1 | 7/2014 | Martin et al. |
| 2014/0194999 A1 | 7/2014 | Orbay et al. |
| 2014/0207144 A1 | 7/2014 | Lee et al. |
| 2014/0249537 A1 | 9/2014 | Wong et al. |
| 2014/0257308 A1 | 9/2014 | Johannaber |
| 2014/0257509 A1 | 9/2014 | Dacosta et al. |
| 2014/0276815 A1 | 9/2014 | Riccione |
| 2014/0276853 A1 | 9/2014 | Long et al. |
| 2014/0277176 A1 | 9/2014 | Buchanan et al. |
| 2014/0277214 A1 | 9/2014 | Helenbolt et al. |
| 2014/0288562 A1 | 9/2014 | Von Zabern et al. |
| 2014/0296995 A1 | 10/2014 | Reiley et al. |
| 2014/0303621 A1 | 10/2014 | Gerold et al. |
| 2014/0336658 A1 | 11/2014 | Luna et al. |
| 2014/0343555 A1 | 11/2014 | Russi et al. |
| 2014/0350561 A1 | 11/2014 | Dacosta et al. |
| 2015/0032168 A1 | 1/2015 | Orsak et al. |
| 2015/0045801 A1 | 2/2015 | Axelson, Jr. et al. |
| 2015/0045839 A1 | 2/2015 | Dacosta et al. |
| 2015/0051650 A1 | 2/2015 | Verstreken et al. |
| 2015/0057667 A1 | 2/2015 | Ammann et al. |
| 2015/0066094 A1 | 3/2015 | Prandi et al. |
| 2015/0112446 A1 | 4/2015 | Melamed et al. |
| 2015/0119944 A1 | 4/2015 | Geldwert |
| 2015/0142064 A1 | 5/2015 | Perez et al. |
| 2015/0150608 A1 | 6/2015 | Sammarco |
| 2015/0182273 A1 | 7/2015 | Stemniski et al. |
| 2015/0223851 A1 | 8/2015 | Hill et al. |
| 2015/0245858 A1 | 9/2015 | Weiner et al. |
| 2016/0015426 A1 | 1/2016 | Dayton |
| 2016/0022315 A1 | 1/2016 | Soffiatti et al. |
| 2016/0135858 A1 | 5/2016 | Dacosta et al. |
| 2016/0151165 A1 | 6/2016 | Fallin et al. |
| 2016/0175089 A1 | 6/2016 | Fallin et al. |
| 2016/0192950 A1 | 7/2016 | Dayton et al. |
| 2016/0199076 A1 | 7/2016 | Fallin et al. |
| 2016/0213384 A1 | 7/2016 | Fallin et al. |
| 2016/0235414 A1 | 8/2016 | Hatch et al. |
| 2016/0242791 A1 | 8/2016 | Fallin et al. |
| 2016/0256204 A1 | 9/2016 | Patel et al. |
| 2016/0324532 A1 | 11/2016 | Montoya et al. |
| 2016/0354127 A1 | 12/2016 | Lundquist et al. |
| 2017/0042598 A1 | 2/2017 | Santrock et al. |
| 2017/0042599 A1 | 2/2017 | Bays et al. |
| 2017/0143511 A1 | 5/2017 | Cachia |
| 2017/0164989 A1 | 6/2017 | Weiner et al. |
| 2018/0132868 A1 | 5/2018 | Dacosta et al. |
| 2018/0344334 A1 | 12/2018 | Kim et al. |

FOREIGN PATENT DOCUMENTS

| | | |
|---|---|---|
| CA | 2854997 A1 | 5/2013 |
| CH | 695846 A5 | 9/2006 |
| CN | 2930668 Y | 8/2007 |
| CN | 201558162 U | 8/2010 |
| CN | 201572172 U | 9/2010 |
| CN | 201586060 U | 9/2010 |
| CN | 201912210 U | 8/2011 |
| CN | 101237835 B | 11/2012 |
| CN | 202801773 U | 3/2013 |
| CN | 103462675 A | 12/2013 |
| CN | 103505276 A | 1/2014 |
| CN | 203458450 U | 3/2014 |
| CN | 103735306 A | 4/2014 |
| CN | 102860860 B | 5/2014 |
| CN | 203576647 U | 5/2014 |
| CN | 104490460 A | 4/2015 |
| CN | 104510523 A | 4/2015 |
| CN | 104523327 A | 4/2015 |
| CN | 104546102 A | 4/2015 |
| CN | 204379413 U | 6/2015 |
| CN | 204410951 U | 6/2015 |
| CN | 204428143 U | 7/2015 |
| CN | 204428144 U | 7/2015 |
| CN | 204428145 U | 7/2015 |
| CN | 204446081 U | 7/2015 |
| DE | 202006010241 U1 | 3/2007 |
| DE | 102007053058 B3 | 4/2009 |
| EP | 685206 B1 | 9/2000 |
| EP | 1508316 B1 | 5/2007 |
| EP | 1897509 B1 | 7/2009 |
| EP | 2124772 A1 | 12/2009 |
| EP | 2124832 B1 | 8/2012 |
| EP | 2632349 A1 | 9/2013 |

(56) References Cited

FOREIGN PATENT DOCUMENTS

| | | |
|---|---|---|
| EP | 2665428 A1 | 11/2013 |
| EP | 2742878 A1 | 6/2014 |
| EP | 2750617 A1 | 7/2014 |
| EP | 2849684 A1 | 3/2015 |
| EP | 2624764 B1 | 12/2015 |
| EP | 3023068 A2 | 5/2016 |
| FR | 2362616 A1 | 3/1978 |
| FR | 2764183 B1 | 11/1999 |
| FR | 2953120 B1 | 1/2012 |
| FR | 3030221 A1 | 6/2016 |
| GB | 2154143 A | 9/1985 |
| GB | 2154144 A | 9/1985 |
| GB | 2334214 B | 1/2003 |
| IN | 200903719 P1 | 6/2009 |
| IN | 200904479 P2 | 5/2010 |
| IN | 140/DELNP/2012 P1 | 2/2013 |
| IN | 2004/KOLNP/2013 P2 | 11/2013 |
| JP | S635739 A | 1/1988 |
| JP | H0531116 A | 2/1993 |
| JP | 2004174265 A | 6/2004 |
| JP | 2006158972 A | 6/2006 |
| JP | 4134243 B2 | 8/2008 |
| JP | 2008537498 A | 9/2008 |
| JP | 4162380 B2 | 10/2008 |
| JP | 2011092405 A | 5/2011 |
| JP | 2011523889 A | 8/2011 |
| JP | 4796943 B2 | 10/2011 |
| JP | 5466647 B2 | 4/2014 |
| JP | 2014511207 A | 5/2014 |
| JP | 2014521384 A | 8/2014 |
| JP | 5628875 B2 | 11/2014 |
| KR | 100904142 B1 | 6/2009 |
| MD | 756 Z | 11/2014 |
| RU | 2098036 C1 | 12/1997 |
| RU | 2195892 C2 | 1/2003 |
| RU | 2320287 C1 | 3/2008 |
| RU | 2321366 C2 | 4/2008 |
| RU | 2321369 C1 | 4/2008 |
| RU | 2346663 C2 | 2/2009 |
| RU | 2412662 C1 | 2/2011 |
| SU | 1333328 A2 | 8/1987 |
| WO | 0166022 A1 | 9/2001 |
| WO | 03075775 A1 | 9/2003 |
| WO | 2004089227 A2 | 10/2004 |
| WO | 2008051064 A1 | 5/2008 |
| WO | 2009029798 A1 | 3/2009 |
| WO | 2009032101 A2 | 3/2009 |
| WO | 2011037885 A1 | 3/2011 |
| WO | 2012029008 A1 | 3/2012 |
| WO | 2013090392 A1 | 6/2013 |
| WO | 2013134387 A1 | 9/2013 |
| WO | 2013169475 A1 | 11/2013 |
| WO | 2014020561 A1 | 2/2014 |
| WO | 2014022055 A1 | 2/2014 |
| WO | 2014035991 A1 | 3/2014 |
| WO | 2014085882 A1 | 6/2014 |
| WO | 2014147099 A1 | 9/2014 |
| WO | 2014152219 A2 | 9/2014 |
| WO | 2014152535 A1 | 9/2014 |
| WO | 2014177783 A1 | 11/2014 |
| WO | 2014200017 A1 | 12/2014 |
| WO | 2015094409 A1 | 6/2015 |
| WO | 2015105880 A1 | 7/2015 |
| WO | 2015127515 A2 | 9/2015 |
| WO | 2016134160 A1 | 8/2016 |

OTHER PUBLICATIONS

Saltzman et al., "Prospective Controlled Trial of Star Total Ankle Replacement Versus Ankle Fusion: Initial Results," Foot & Ankle International, vol. 30, No. 7, Jul. 2009, pp. 579-596.

Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).

Scranton Jr. et al, "Anatomic Variations in the First Ray: Part I. Anatomic Aspects Related to Bunion Surgery," Clinical Orthopaedics and Related Research, vol. 151, Sep. 1980, pp. 244-255.

Siddiqui et al. "Fixation Of Metatarsal Fracture With Bone Plate In A Dromedary Heifer," Open Veterinary Journal, vol. 3, No. 1, 2013, pp. 17-20.

Sidekick Stealth Rearfoot Fixator, Wright Medical Technology, Surgical Technique, Dec. 2, 2013, 20 pages.

Simpson et al., "Computer-Assisted Distraction Ostegogenesis By Ilizarov's Method," International Journal of Medical Robots and Computer Assisted Surgery, vol. 4, No. 4, Dec. 2008, pp. 310-320, (Abstract Only).

Small Bone External Fixation System, Acumed, Surgical Technique, Effective date Sep. 2014, 8 pages.

"Smith & Nephew scores a Hat-Trick with its entry into the high-growth hammer toe repair market," Smith & Nephew, Jul. 31, 2014, 2 pages.

Stableloc External Fixation System, Acumed, Product Overview, Effective date Sep. 2015, 4 pages.

Stahl et al., "Derotation Of Post-Traumatic Femoral Deformities By Closed Intramedullary Sawing," Injury, vol. 37, No. 2, Feb. 2006, pp. 145-151, (Abstract Only).

Talbot et al., "Assessing Sesamoid Subluxation: How Good is the AP Radiograph?," Foot and Ankle International, vol. 19, No. 8, Aug. 1998, pp. 547-554.

TempFix Spanning the Ankle Joint Half Pin and Transfixing Pin Techniques, Biomet Orthopedics, Surgical Technique, 2012, 16 pages.

Tricot et al., "3D-corrective osteotomy using surgical guides for posttraumatic distal humeral deformity," Acta Orthopaedica Belgica, vol. 78, No. 4, 2012, pp. 538-542.

Vitek et al., "Die Behandlung des Hallux rigidus mit Cheilektomie und Akin-Moberg-Osteotomie unter Verwendung einer neuen Schnittlehre und eines neuen Schraubensystems," Orthopädische Praxis, vol. 44, Nov. 2008, pp. 563-566, including English Abstract on p. 564.

Vitek, "Neue Techniken in der Fußchirurgie Das V-tek-System," ABW Wissenschaftsverlag GmbH, 2009, 11 pages, including English Abstract.

Weber et al., "A Simple System For Navigation Of Bone Alignment Osteotomies Of The Tibia," International Congress Series, vol. 1268, Jan. 2004, pp. 608-613, (Abstract Only).

Weil et al., "Anatomic Plantar Plate Repair Using the Weil Metatarsal Osteotomy Approach," Foot & Ankle Specialist, vol. 4, No. 3, 2011, pp. 145-150.

Alvine et al., "Peg and Dowel Fusion of the Proximal Interphalangeal Joint," Foot & Ankle, vol. 1, No. 2, 1980, pp. 90-94.

Bednarz et al., "Modified Lapidus Procedure for the Treatment of Hypermobile Hallux Valgus," Foot & Ankle International, vol. 21, No. 10, Oct. 2000, pp. 816-821.

Carr et al., "Correctional Osteotomy for Metatarsus Primus Varus and Hallux Valgus," The Journal of Bone and Joint Surgery, vol. 50-A, No. 7, Oct. 1968, pp. 1353-1367.

Coetzee et al., "The Lapidus Procedure: A Prospective Cohort Outcome Study," Foot & Ankle International, vol. 25, No. 8, Aug. 2004, pp. 526-531.

Doty et al., "Hallux valgus and hypermobility of the first ray: facts and fiction," International Orthopaedics, vol. 37, 2013, pp. 1655-1660.

Galli et al., "Enhanced Lapidus Arthrodesis: Crossed Screw Technique With Middle Cuneiform Fixation Further Reduces Sagittal Mobility," The Journal of Foot & Ankle Surgery, vol. 54, vol. 3, May/Jun. 2015, published online: Nov. 21, 2014, pp. 437-440.

Lapidus, "The Author's Bunion Operation From 1931 to 1959," Clinical Orthopaedics, vol. 16, 1960, pp. 119-135.

Osher et al., "Accurate Determination of Relative Metatarsal Protrusion with a Small Intermetatarsal Angle: A Novel Simplified Method," The Journal of Foot & Ankle Surgery, vol. 53, No. 5, Sep./Oct. 2014, published online: Jun. 3, 2014, pp. 548-556.

(56) References Cited

OTHER PUBLICATIONS

Patel et al., "Modified Lapidus Arthrodesis: Rate of Nonunion in 227 Cases," The Journal of Foot & Ankle Surgery, vol. 43, No. 1, Jan./Feb. 2004, pp. 37-42.
Toth et al., "The Effect of First Ray Shortening in the Development of Metatarsalgia in the Second Through Fourth Rays After Metatarsal Osteotomy," Foot & Ankle International, vol. 28, No. 1, Jan. 2007, pp. 61-63.
Dayton et al., "Comparison of the Mechanical Characteristics of a Universal Small Biplane Plating Technique Without Compression Screw and Single Anatomic Plate With Compression Screw," The Journal of Foot & Ankle Surgery, vol. 55, No. 3, May/Jun. 2016, published online: Feb. 9, 2016, pp. 567-571.
Giannoudis et al., "Hallux Valgus Correction," Practical Procedures in Elective Orthopaedic Surgery, Pelvis and Lower Extremity, Chapter 38, 2012, 22 pages.
Greiner, "The Jargon of Pedal Movements," Foot & Ankle International, vol. 28, No. 1, Jan. 2007, pp. 109-125.
Groves, "Functional Position Joint Sectioning: Pre-Load Method for Lapidus Arthrodesis," The Podiatry Institute, Update 2015, Chapter 6, 2015, pp. 23-29.
Hardy et al., "Observations on Hallux Valgus," The Journal of Bone and Joint Surgery, vol. 33B, No. 3, Aug. 1951, pp. 376-391.
Holmes, Jr., "Correction of the Intermetatarsal Angle Component of Hallux Valgus Using Fiberwire-Attached Endo-buttons," Revista Intemacional de Ciencias Podologicas, vol. 6, No. 2, 2012, pp. 73-79.
Integra, "Integra Large Qwix Positioning and Fixation Screw, Surgical Technique," 2012, 16 pages.
Kilmartin et al., "Combined rotation scarf and Akin osteotomies for hallux valgus: a patient focused 9 year follow up of 50 patients," Journal of Foot and Ankle Research, vol. 3, No. 2, 2010, 12 pages.
Lee et al., "Technique Tip: Lateral Soft-Tissue Release for Correction of Hallux Valgus Through a Medial Incision Using A Dorsal Flap Over the First Metatarsal," Foot & Ankle International, vol. 28, No. 8, Aug. 2007, pp. 949-951.
Mote et al., "First Metatarsal-Cuneiform Arthrodesis for the Treatment of First Ray Pathology: A Technical Guide," JFAS Techniques Guide, vol. 48, No. 5, Sep./Oct. 2009, pp. 593-601.
Myerson, "Cuneiform-Metatarsal Arthrodesis," The Foot and Ankle, Chapter 9, 1997, pp. 107-117.
Sammarco, "Surgical Strategies: Mau Osteotomy for Correction of Moderate and Severe Hallux Valgus Deformity," Foot & Ankle International, vol. 28, No. 7, Jul. 2007, pp. 857-864.
Schon et al., "Cuneiform-Metatarsal Arthrodesis for Hallux Valgus,"The Foot and Ankle, Second Edition, Chapter 8, 2002, pp. 99-117.
Sokoloff, "Lapidus Procedure," Textbook of Bunion Surgery, Chapter 15, 1981, pp. 277-287.
Stamatis et al., "Mini Locking Plate as "Medial Buttress" for Oblique Osteotomy for Hallux Valgus," Foot & Ankle International, vol. 31, No. 10, Oct. 2010, pp. 920-922.
Stewart, "Use for BME Speed Nitinol Staple Fixation for the Lapidus Procedure," date unknown, 1 page.
Wukich et al., "Hypermobility of the First Tarsometatarsal Joint," Foot and Ankle Clinics, vol. 10, No. 1, Mar. 2005, pp. 157-166.
Dayton et al., "Biwinged Excision for Round Pedal Lesions," The Journal of Foot and Ankle Surgery, vol. 35, No. 3, 1996, pp. 244-249.
Dayton et al., "Medial Incision Approach to the First Metatarsophalangeal Joint," The Journal of Foot and Ankle Surgery, vol. 40, No. 6, Nov./Dec. 2001, pp. 414-417.
Dayton et al., "Reduction of the Intermetatarsal Angle after First Metatarsophalangeal Joint Arthrodesis in Patients with Moderate and Severe Metatarsus Primus Adductus," The Journal of Foot and Ankle Surgery, vol. 41, No. 5, Sep./Oct. 2002, pp. 316-319.
Dayton et al., "Use of the Z Osteotomy for Tailor Bunionectomy," The Journal of Foot and Ankle Surgery, vol. 42, No. 3, May/Jun. 2003, pp. 167-169.
Dayton et al., "Early Weightbearing After First Metatarsophalangeal Joint Arthrodesis: A Retrospective Observational Case Analysis," The Journal of Foot and Ankle Surgery, vol. 43, No. 3, May/Jun. 2004, pp. 156-159.
"Accu-Cut Osteotomy Guide System," BioPro, Brochure, Oct. 2018, 2 pages.
"Acumed Osteotomiesystem Operationstechnik," Acumed, 2014, 19 pages (including 3 pages English translation).
Albano et al., "Biomechanical Study of Transcortical or Transtrabecular Bone Fixation of Patellar Tendon Graft wih Bioabsorbable Pins in ACL Reconstruction in Sheep," Revista Brasileira de Ortopedia (Rev Bras Ortop.) vol. 47, No. 1, 2012, pp. 43-49.
Anderson et al., "Uncemented Star Total Ankle Prostheses," The Journal of Bone and Joint Surgery, vol. 86(1, Suppl 2), Sep. 2004, pp. 103-111, (Abstract Only).
Blomer, "Knieendoprothetik—Herstellerische Probleme und technologische Entwicklungen," Orthopade, vol. 29, 2000, pp. 688-696, including English Abstract on p. 689.
Bouaicha et al., "Fixation of Maximal Shift Scarf Osteotomy with Inside-Out Plating: Technique Tip," Foot & Ankle International, vol. 32, No. 5, May 2011, pp. 567-569.
Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.
Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, vol. 53, 2014, pp. 584-587.
Dayton et al., "Relationship Of Frontal Plane Rotation Of First Metatarsal To Proximal Articular Set Angle And Hallux Alignment In Patients Undergoing Tarsometatarsal Arthrodesis For Hallux Abducto Valgus: A Case Series And Critical Review Of The Literature," The Journal of Foot and Ankle Surgery, vol. 52, No. 3, May/Jun. 2013, pp. 348-354.
Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.
De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.
DiDomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.
Dobbe et al. "Patient-Tailored Plate For Bone Fixation And Accurate 3D Positioning In Corrective Osteotomy," Medical and Biological Engineering and Computing, vol. 51, No. 1-2, Feb. 2013, pp. 19-27, (Abstract Only).
EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.
"Futura Forefoot Implant Arthroplasty Products," Tornier, Inc., 2008, 14 pages.
Garthwait, "Accu-Cut System Facilitates Enhanced Precision," Podiatry Today, vol. 18, No. 6, Jun. 2005, 6 pages.
Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.
Gotte, "Entwicklung eines Assistenzrobotersystems für die Knieendoprothetik," Forschungsberichte, Technische Universitat Munchen, 165, 2002, 11 pages, including partial English Translation.
Gregg et al., "Plantar plate repair and Weil osteotomy for metatarsophalangeal joint instability," Foot and Ankle Surgery, vol. 13, 2007, pp. 116-121.

(56) References Cited

OTHER PUBLICATIONS

Grondal et al., "A Guide Plate for Accurate Positioning of First Metatarsophalangeal Joint during Fusion," Operative Orthopädie Und Traumatologie, vol. 16, No. 2, 2004, pp. 167-178 (Abstract Only).
"Hat-Trick Lesser Toe Repair System," Smith & Nephew, Brochure, Aug. 2014, 12 pages.
"Hat-Trick Lesser Toe Repair System, Foot and Ankle Technique Guide, Metatarsal Shortening Osteotomy Surgical Technique," Smith & Nephew, 2014, 16 pages.
Hetherington et al., "Evaluation of surgical experience and the use of an osteotomy guide on the apical angle of an Austin osteotomy," The Foot, vol. 18, 2008, pp. 159-164.
Hirao et al., "Computer assisted planning and custom-made surgical guide for malunited pronation deformity after first metatarsophalangeal joint arthrodesis in rheumatoid arthritis: A case report," Computer Aided Surgery, vol. 19, Nos. 1-3, 2014, pp. 13-19.
"Hoffmann II Compact External Fixation System," Stryker, Brochure, Literature No. 5075-1-500, 2006, 12 pages.
"Hoffmann II Micro Lengthener," Stryker, Operative Technique, Literature No. 5075-2-002, 2008, 12 pages.
"Hoffmann Small System External Fixator Orthopedic Instruments," Stryker, retrieved Dec. 19, 2014, from the Internet: <http://www.alibaba.com/product-detail/Stryker-Hoffmann-Small-System-External-Fixator_1438850129.html>, 3 pages.
Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.
"Lag Screw Target Bow," Stryker Leibinger GmbH & Co. KG, Germany 2004, 8 pages.
Lieske et al., "Implantation einer Sprunggelenktotalendo-prothese vom Typ Salto 2," Operative Orthopädie und Traumatologie, vol. 26, No. 4, 2014, pp. 401-413, including English Abstract on p. 403.
MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.
Magin, "Computernavigierter Gelenkersatz am Knie mit dem Orthopilot," Operative Orthopädie und Traumatologie, vol. 22, No. 1, 2010, pp. 63-80, including English Abstract on p. 64.
Magin, "Die belastungsstabile Lapidus-Arthrodese bei Halluxvalgus-Deformität mittels IVP-Plattenfixateur (V-TEK-System)," Operative Orthopädie und Traumatologie, vol. 26, No. 2, 2014, pp. 184-195, including English Abstract on p. 186.
Michelangelo Bunion System, Surgical Technique, Instratek Incorporated, publication date unknown, 4 pages.
Mini Joint Distractor, Arthrex, retrieved Dec. 19, 2014, from the Internet: <http://www.arthrex.com/foot-ankle/mini-joint-distractor/products>, 2 pages.
MiniRail System, Small Bone Innovations, Surgical Technique, 2010, 24 pages.
Miyake et al., "Three-Dimensional Corrective Osteotomy for Malunited Diaphyseal Forearm Fractures Using Custom-Made Surgical Guides Based on Computer Simulation," JBJS Essential Surgical Techniques, vol. 2, No. 4, 2012, 11 pages.
Modular Rail System: External Fixator, Smith & Nephew, Surgical Technique, 2013, 44 pages.
Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).
Moore et al., "Effect Of Ankle Flexion Angle On Axial Alignment Of Total Ankle Replacement," Foot and Ankle International, vol. 31, No. 12, Dec. 2010, pp. 1093-1098, (Abstract Only).
Mortier et al., "Axial Rotation of the First Metatarsal Head in a Normal Population and Hallux Valgus Patients," Orthopaedics and Traumatology: Surgery and Research, vol. 98, 2012, pp. 677-683.

Nagy et al., "The AO Ulnar Shortening Osteotomy System Indications and Surgical Technique," Journal of Wrist Surgery, vol. 3, No. 2, 2014, pp. 91-97.
NexFix from Nexa Orthopedics, MetaFix I from Merete Medical, Inc. and The BioPro Lower Extremities from BioPro, found in Foot & Ankle International Journal, vol. 28, No. 1, Jan. 2007, 4 pages.
Odenbring et al., "A guide instrument for high tibial osteotomy," Acta Orthopaedica Scandinavica, vol. 60, No. 4, 1989, pp. 449-451.
Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.
Otsuki et al., "Developing a novel custom cutting guide for curved per-acetabular osteotomy," International Orthopaedics (SICOT), vol. 37, 2013, pp. 1033-1038.
"Patient to Patient Precision, Accu-Cut, Osteotomy Guide System," BioPro, Foot & Ankle International Journal, vol. 23, No. 8, Aug. 2002, 2 pages.
Peters et al., "Flexor Hallucis Longus Tendon Laceration as a Complication of Total Ankle Arthroplasty," Foot & Ankle International, vol. 34, No. 1, 2013, pp. 148-149.
"Prophecy Inbone Preoperative Navigation Guides," Wright Medical Technology, Inc., Nov. 2013, 6 pages.
"Rayhack Ulnar Shortening Generation II Low-Profile Locking System Surgical Technique," Wright Medical Technology, Inc., Dec. 2013, 20 pages.
Defendant Fusion Orthopedics LLC's Invalidity Contentions, No. CV-22-00490-PHX-SRB, US District Court for the District of Arizona, Aug. 27, 2022, 41 pages.
Prior Art Publications, Exhibit A of Defendant Fusion Orthopedics LLC's Invalidity Contentions, No. CV-22-00490-PHX-SRB, US District Court for the District of Arizona, Aug. 27, 2022, 3 pages.
Claim Chart for Fishco, "Making the Lapidus Easy," The Podiatry Institute (Apr. 2014), Exhibit B1 of Defendant Fusion Orthopedics LLC's Invalidity Contentions, No. CV-22-00490-PHX-SRB, US District Court for the District of Arizona, Aug. 27, 2022, 97 pages.
Claim Chart for Fishco, "A Straightforward Guide to the Lapidus Bunionectomy," HMP Global (Sep. 6, 2013), Exhibit B2 of Defendant Fusion Orthopedics LLC's Invalidity Contentions, No. CV-22-00490-PHX-SRB, US District Court for the District of Arizona, Aug. 27, 2022, 67 pages.
Claim Chart for Groves, "Functional Position Joint Sectioning: Pre-Load Method for Lapidus Arthrodesis," Update 2015: Proceedings of the Annual Meeting of the Podiatry Institute, Chpt. 6, pp. 23-29 (Apr. 2015), Exhibit B3 of Defendant Fusion Orthopedics LLC's Invalidity Contentions, No. CV-22-00490-PHX-SRB, US District Court for the District of Arizona, Aug. 27, 2022, 151 pages.
Claim Chart for Mote, "First Metatarsal-Cuneiform Arthrodesis for the Treatment of First Ray Pathology: A Technical Guide," The Journal Foot & Ankle Surgery (Sep. 1, 2009), Exhibit B5 of Defendant Fusion Orthopedics LLC's Invalidity Contentions, No. CV-22-00490-PHX-SRB, US District Court for the District of Arizona, Aug. 27, 2022, 21 pages.
Claim Chart for U.S. Pat. No. 10,376,268 to Fallin et al., entitled "Indexed Tri-Planar Osteotomy Guide and Method," issued Aug. 13, 2019, Exhibit B6 of Defendant Fusion Orthopedics LLC's Invalidity Contentions, No. CV-22-00490-PHX-SRB, US District Court for the District of Arizona, Aug. 27, 2022, 155 pages.
Claim Chart for U.S. Pat. No. 8,282,645 to Lawrence et al., entitled "Metatarsal Bone Implant Cutting Guide," issued Jan. 18, 2010, Exhibit B7 of Defendant Fusion Orthopedics LLC's Invalidity Contentions, No. CV-22-00490-PHX-SRB, US District Court for the District of Arizona, Aug. 27, 2022, 76 pages.
Claim Chart for U.S. Pat. No. 9,452,057 to Dacosta et al., entitled "Bone Implants and Cutting Apparatuses and Methods," issued Apr. 8, 2011, Exhibit B8 of Defendant Fusion Orthopedics LLC's Invalidity Contentions, No. CV-22-00490-PHX-SRB, US District Court for the District of Arizona, Aug. 27, 2022, 110 pages.
Obviousness Chart, Exhibit C of Defendant Fusion Orthopedics LLC's Invalidity Contentions, No. CV-22-00490-PHX-SRB, US District Court for the District of Arizona, Aug. 27, 2022, 153 pages.
"Foot and Ankle Instrument Set," Smith & Nephew, 2013, 2 pages.

(56) References Cited

OTHER PUBLICATIONS

"Lapidus Pearls: Gaining Joint Exposure to Decrease Non-Union," Youtube, Retrieved online from <https://www.youtube com/watch?v=-jqJyE7pj-Y>, dated Nov. 2, 2009, 3 pages.

"Reconstructive Surgery of the Foot & Ankle," The Podiatry Institute, Update 2015, Conference Program, May 2015, 28 pages.

"Speed Continuous Active Compression Implant," BioMedical Enterprises, Inc., A120-029 Rev. 3, 2013, 4 pages.

"Visionaire: Patient Matched Cutting Blocks Surgical Procedure," Smith & Nephew, Inc., 2009, 2 pages.

Arthrex, "Comprehensive Foot System," Retrieved online from <https://www.arthrex.com/resources/animation/8U3iaPvY6kO8bwFAwZF50Q/comprehensive-foot-system?referringTeam=foot_and_ankle>, dated Aug. 27, 2013, 3 pages.

Baravarian, "Why the Lapidus Procedure is Ideal for Bunions," Podiatry Today, Retrieved online from <https://www.hmpglobal-learhmpgloballe.com/site/podipodi/article/5542>, dated May 2006, 8 pages.

Bauer et al., "Offset-V Osteotomy of the First Metatarsal Shaft in Hallux Abducto Valgus," McGlamry's Comprehensive Textbook of Foot and Ankle Surgery, Fourth Edition, vol. 1, Chapter 29, 2013, 26 pages.

Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.

Coughlin, "Fixation of the Lapidus Arthrodesis with a Plantar Interfragmentary Screw and Medial Low Profile Locking Plate,"Orthopaedics and Traumatology, vol. 7, 1999, pp. 133-143.

Dayton et al., "Observed Changes in Radiographic Measurements of the First Ray after Frontal Plane Rotation of the First Metatarsal in a Cadaveric Foot Model," The Journal of Foot & Ankle Surgery, vol. 53, 2014, pp. 274-278.

Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot & Ankle Surgery, 2013, Article in Press, Mar. 1, 2013, 7 pages.

DiDomenico et al., "Lapidus Bunionectomy: First Metatarsal-Cuneiform Arthrodesis," McGlamry's Comprehensive Textbook of Foot and Ankle Surgery, Fourth Edition, vol. 1, Chapter 31, 2013, 24 pages.

Fallin et al., US Provisional Application Entitled Indexed Tri-Planar Osteotomy Guide and Method, U.S. Appl. No. 62/118,378, filed Feb. 19, 2015, 62 pages.

Fishco, "A Straightforward Guide To The Lapidus Bunionectomy,"Podiatry Today, Retrieved online from <https://www.hmpgloballearningnetwork.com/site/podiatry/blogged/straightforward-guide-lapidus-bunionectomy>, dated Sep. 6, 2013, 5 pages.

Fishco, "Making the Lapidus Easy," The Podiatry Institute, Update 2014, Chapter 14, 2014, pp. 91-93.

Fleming et al., "Results of Modified Lapidus Arthrodesis Procedure Using Medial Eminence as an Interpositional Autograft," The Journal of Foot & Ankle Surgery, vol. 50, 2011, pp. 272-275.

Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.

Gerard et al., "The Modified Lapidus Procedure," Orthopedics, vol. 31, No. 3, Mar. 2008, 7 pages.

Dayton et al., "Dorsal Suspension Stitch: An Alternative Stabilization After Flexor Tenotomy for Flexible Hammer Digit Syndrome," The Journal of Foot and Ankle Surgery, vol. 48, No. 5, Sep./Oct. 2009, pp. 602-605.

Dayton et al., "The Extended Knee Hemilithotomy Position for Gastrocnemius Recession," The Journal of Foot and Ankle Surgery, vol. 49, 2010, pp. 214-216.

Wienke et al., "Bone Stimulation For Nonunions: What the Evidence Reveals," Podiatry Today, vol. 24, No. 9, Sep. 2011, pp. 52-57.

Dayton et al., "Hallux Varus as Complication of Foot Compartment Syndrome," The Journal of Foot and Ankle Surgery, vol. 50, 2011, pp. 504-506.

Dayton et al., "Measurement of Mid-Calcaneal Length on Plain Radiographs: Reliability of a New Method," Foot and Ankle Specialist, vol. 4, No. 5, Oct. 2011, pp. 280-283.

Dayton et al., "A User-Friendly Method of Pin Site Management for External Fixators," Foot and Ankle Specialist, Sep. 16, 2011, 4 pages.

Dayton et al., "Effectiveness of a Locking Plate in Preserving Midcalcaneal Length and Positional Outcome after Evans Calcaneal Osteotomy: A Retrospective Pilot Study," The Journal of Foot and Ankle Surgery, vol. 52, 2013, pp. 710-713.

Dayton et al., "Does Postoperative Showering or Bathing of a Surgical Site Increase the Incidence of Infection? A Systematic Review of the Literature," The Journal of Foot and Ankle Surgery, vol. 52, 2013, pp. 612-614.

Dayton et al., "Technique for Minimally Invasive Reduction of Calcaneal Fractures Using Small Bilateral External Fixation," The Journal of Foot and Ankle Surgery, Article in Press, 2014, 7 pages.

Dayton et al., "Clarification of the Anatomic Definition of the Bunion Deformity," The Journal of Foot and Ankle Surgery, vol. 53, 2014, pp. 160-163.

Dayton et al., "Observed Changes in Radiographic Measurements of the First Ray after Frontal Plane Rotation of the First Metatarsal in a Cadaveric Foot Model," The Journal of Foot and Ankle Surgery, Article in Press, 2014, 5 pages.

Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.

Dayton et al., "Reduction of the Intermetatarsal Angle after First Metatarsal Phalangeal Joint Arthrodesis: A Systematic Review," The Journal of Foot and Ankle Surgery, Article in Press, 2014, 4 pages.

Feilmeier et al., "Reduction of Intermetatarsal Angle after First Metatarsophalangeal Joint Arthrodesis in Patients with Hallux Valgus," The Journal of Foot and Ankle Surgery, vol. 53, 2014, pp. 29-31.

Dayton et al., "Principles of Management of Growth Plate Fractures in the Foot and Ankle," Clinics in Podiatric Medicine and Surgery, Pediatric Foot Deformities, Oct. 2013, 17 pages.

Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, Article in Press, 2014, 4 pages.

Rodriguez et al., "Ilizarov method of fixation for the management of pilon and distal tibial fractures in the compromised diabetic patient: A technique guide," The Foot and Ankle Journal Online, vol. 7, No. 2, 2014, 9 pages.

Feilmeier et al., "Incidence of Surgical Site Infection in the Foot and Ankle with Early Exposure and Showering of Surgical Sites: A Prospective Observation," The Journal of Foot and Ankle Surgery, vol. 53, 2014, pp. 173-175.

Catanese et al., "Measuring Sesamoid Position in Hallux Valgus: When Is the Sesamoid Axial View Necessary," Foot and Ankle Specialist, 2014, 3 pages.

Dayton et al., "Comparison of Complications for Internal and External Fixation for Charcot Reconstruction: A Systematic Review," The Journal of Foot and Ankle Surgery, Article in Press, 2015, 4 pages.

Dayton et al., "A new triplanar paradigm for bunion management," Lower Extremity Review, Apr. 2015, 9 pages.

Dayton et al., "American College of Foot and Ankle Surgeons' Clinical Consensus Statement: Perioperative Prophylactic Antibiotic Use in Clean Elective Foot Surgery," The Journal of Foot and Ankle Surgery, Article in Press, 2015, 7 pages.

Dayton et al., "Complications of Metatarsal Suture Techniques for Bunion Correction: A Systematic Review of the Literature," The Journal of Foot and Ankle Surgery, Article in Press, 2015, 3 pages.

(56) References Cited

OTHER PUBLICATIONS

DeCarbo et al., "The Weil Osteotomy: A Refresher," Techniques in Foot and Ankle Surgery, vol. 13, No. 4, Dec. 2014, pp. 191-198.
DeCarbo et al., "Resurfacing Interpositional Arthroplasty for Degenerative Joint Diseas of the First Metatarsalphalangeal Joint," Podiatry Management, Jan. 2013, pp. 137-142.
DeCarbo et al., "Locking Plates: Do They Prevent Complications?," Podiatry Today, Apr. 2014, 7 pages.
Easley et al., "Current Concepts Review: Hallux Valgus Part II: Operative Treatment," Foot and Ankle International, vol. 28, No. 6, Jun. 2007, pp. 748-758.
Kim et lal., "A Multicenter Retrospective Review of Outcomes for Arthrodesis, Hemi-Metallic Joint Implant, and Resectional Arthroplasty in the Surgical Treatment of End-Stage Hallux Rigidus," The Journal of Foot and Ankle Surgery, vol. 51, 2012, pp. 50-56.
Easley et al., "Current Concepts Review: Hallux Valgus Part I: Pathomechanics, Clinical Assessment, and Nonoperative Management," Foot and Ankle International, vol. 28, No. 5, May 2007, pp. 654-659.
Sandhu et al., "Digital Arthrodesis With a One-Piece Memory Nitinol Intramedullary Fixation Device: A Retrospective Review," Foot and Ankle Specialist, vol. 6, No. 5, Oct. 2013, pp. 364-366.
Weber et al., "Use of the First Ray Splay Test to Assess Transverse Plane Instability Before First Metatarsocuneiform Fusion," The Journal of Foot and Ankle Surgery, vol. 45, No. 4, Jul./Aug. 2006, pp. 278-282.
Smith et al., "Opening Wedge Osteotomies for Correction of Hallux Valgus: A Review of Wedge Plate Fixation," Foot and Ankle Specialist, vol. 2, No. 6, Dec. 2009, pp. 277-282.
Easley et al., "What is the Best Treatment for Hallux Valgus?," Evidence-Based Orthopaedics—The Best Answers to Clinical Questions, Chapter 73, 2009, pp. 479-491.
Shurnas et al., "Proximal Metatarsal Opening Wedge Osteotomy," Operative Techniques in Foot and Ankle Surgery, Section I, Chapter 13, 2011, pp. 73-78.
Coetzee et al., "Revision Hallux Valgus Correction," Operative Techniques in Foot and Ankle Surgery, Section I, Chapter 15, 2011, pp. 84-96.
Le et al., "Tarsometatarsal Arthrodesis," Operative Techniques in Foot and Ankle Surgery, Section II, Chapter 40, 2011, pp. 281-285.
Collan et al., "The biomechanics of the first metatarsal bone in hallux valgus: A preliminary study utilizing a weight bearing extremity CT," Foot and Ankle Surgery, vol. 19, 2013, pp. 155-161.
Eustace et al., "Hallux valgus, first metatarsal pronation and collapse of the medial longitudinal arch—a radiological correlation," Skeletal Radiology, vol. 23, 1994, pp. 191-194.
Mizuno et al., "Detorsion Osteotomy of the First Metatarsal Bone in Hallux Valgus," Japanese Orthopaedic Association, Tokyo, 1956; 30:813-819.
Okuda et al., "The Shape of the Lateral Edge of the First Metatarsal Head as a Risk Factor for Recurrence of Hallux Valgus," The Journal of Bone and Joint Surgery, vol. 89, 2007, pp. 2163-2172.
Okuda et al., "Proximal Metatarsal Osteotomy for Hallux Valgus: Comparison of Outcome for Moderate and Severe Deformities, Foot and Ankle International," vol. 29, No. 7, Jul. 2008, pp. 664-670.
D'Amico et al., "Motion of the First Ray: Clarification Through Investigation," Journal of the American Podiatry Association, vol. 69, No. 1, Jan. 1979, pp. 17-23.
Groves, "Operative Report," St. Tammany Parish Hospital, Date of Procedure, Mar. 26, 2014, 2 pages.
Claim Chart for Groves Public Use (Mar. 26, 2014), Exhibit B4 of Defendant Fusion Orthopedics LLC's Invalidity Contentions, No. CV-22-00490-PHX-SRB, US District Court for the District of Arizona, Aug. 27, 2022, 161 pages.
International Patent Application No. PCT/US2016/052087, International Search Report and Written Opinion dated Dec. 20, 2016, 7 pages.
European Patent Application No. 16847367.6, Extended European Search Report dated Apr. 18, 2019, 9 pages.
Yasuda et al., "Proximal Supination Osteotomy of the First Metatarsal for Hallux Valgus," Foot and Ankle International, vol. 36, No. 6, Jun. 2015, pp. 696-704.
Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).
Whipple et al., "Zimmer Herbert Whipple Bone Screw System: Surgical Techniques for Fixation of Scaphoid and Other Small Bone Fractures," Zimmer, 2003, 59 pages.
Wendl et al., "Navigation in der Knieendoprothetik," OP-Journal, vol. 17, 2002, pp. 22-27, including English Abstract.

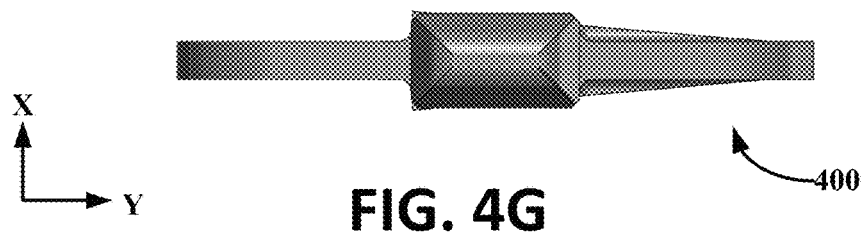
FIG. 4G
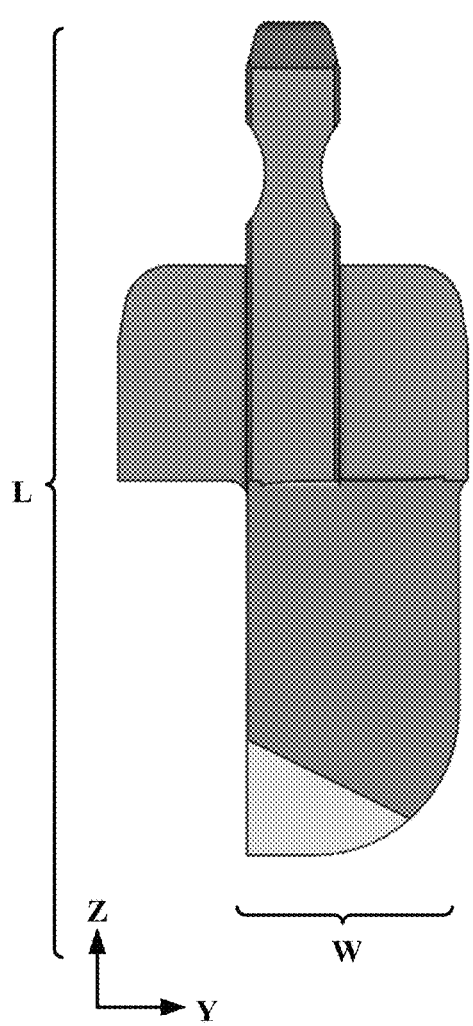
FIG. 4H
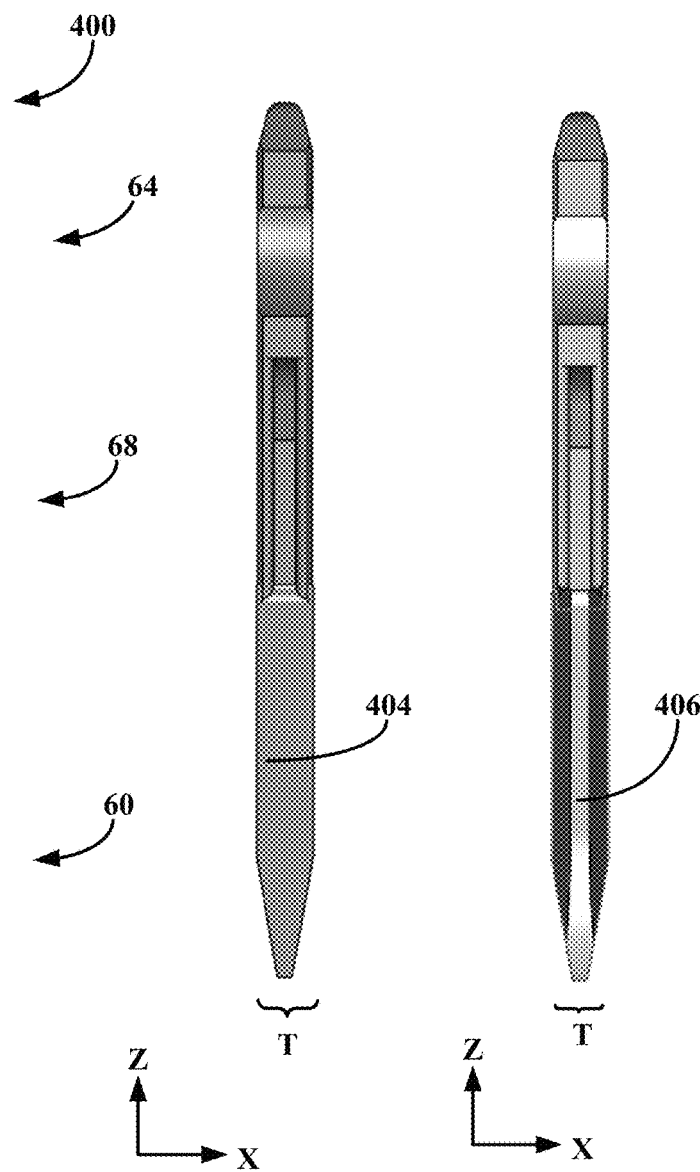
FIG. 4I      FIG. 4J

JOINT SPACER SYSTEMS AND METHODS

CROSS-REFERENCE

This application is a continuation of U.S. patent application Ser. No. 16/750,829, filed Jan. 23, 2020, which is a continuation of U.S. patent application Ser. No. 15/267,531, filed Sep. 16, 2016, and issued as U.S. Pat. No. 10,575,862 on Mar. 3, 2020, which claims the benefit of U.S. Provisional Patent Application No. 62/366,219, filed Jul. 25, 2016, and U.S. Provisional Patent Application No. 62/220,530, filed Sep. 18, 2015. The entire contents of each of these applications are incorporated herein by reference.

TECHNICAL FIELD

This disclosure relates generally to devices and methods for preparing and realigning bones.

BACKGROUND

Bones, such as the bones of a foot, may be anatomically misaligned. In certain circumstances, surgical intervention is required to correctly align the bones to reduce patient discomfort and improve patient quality of life.

SUMMARY

In general, this disclosure is directed to devices and techniques for preparing and realigning one or more bones from an anatomically misaligned position to an anatomically aligned position. In some examples, the devices and techniques are utilized to correct a bunion deformity where a first metatarsal is anatomically misaligned relative to a medial cuneiform and/or second metatarsal. To correct such a misalignment, a system may be utilized that includes a bone preparing guide and a spacer. The bone preparing guide can provide one or more cutting surfaces and/or cutting slots along or through which a cutting instrument can be translated to prepare opposed ends of the first metatarsal and/or medial cuneiform for relative realignment. The spacer can serve as an alignment and/or reference tool for the bone preparing guide.

In some examples, a clinician inserts the spacer into the joint space between the first metatarsal and medial cuneiform. The spacer can have a variety of different configurations, such as a centered insertion portion, an offset insertion portion, a constant thickness, a tapered thickness, or the like. After suitably positioning the spacer, the clinician may insert the bone preparing guide across the joint space, e.g., by installing the bone preparing guide over a portion of the spacer projecting out of the joint space. The clinician can then use the bone preparing guide to cut the end of the first metatarsal and/or the end of the medial cuneiform to facilitate realignment of the bones relative to each other. In some examples, the clinician utilizes a tissue removing instrument location check to check the position and/or orientation of one or more cutting surfaces or slots relative to the bone(s) to be cut before making such cuts. In either case, the clinician may adjust the position of the first metatarsal either before or after making the cuts to achieve realignment of the metatarsal.

In one example, a method for preparing one or more bones is described. The method includes inserting a spacer into a space defined between a first bone and a second bone. The method further involves aligning a bone preparation guide with a portion of the first bone or the second bone while the spacer is inserted into the space, using the spacer as a reference. In addition, the method includes contacting the portion of the first bone or the second bone with a tissue removing instrument using the bone preparation guide to guide the tissue removing instrument.

In another example, a bone preparation guide is described that includes a body and a spacer. The body has a first guide surface to define a first preparing plane and a second guide surface to define a second preparing plane. The first and second guide surfaces are spaced from each other by a distance. The example specifies that a first end extends from the body in a first direction and a second end extends from the body in a second direction, the second direction being different than the first direction, with each of the first end and the second end including a fixation aperture configured to receive a fixation device. The example also specifies that the spacer extends from the body in a third direction, the third direction being different than the first and second directions. The spacer is configured to be placed into a joint space between opposing bones.

In another example, a spacer configured to be inserted into a joint space between first and second opposing bones is described. The spacer includes a first portion configured to extend into the joint space and a second portion, opposite the first portion, configured to extend above the joint space. The spacer also includes an intermediate portion disposed between the first portion and the second portion. The example specifies that the spacer is configured to serve as a reference to position a tissue removing instrument with respect to the first and/or second bone.

The details of one or more examples are set forth in the accompanying drawings and the description below. Other features, objects, and advantages will be apparent from the description and drawings, and from the claims.

BRIEF DESCRIPTION OF THE DRAWINGS

FIGS. 4G-4J illustrate another example configuration of a spacer where the thickness of the spacer varies across the width of the spacer.

Figure 1:
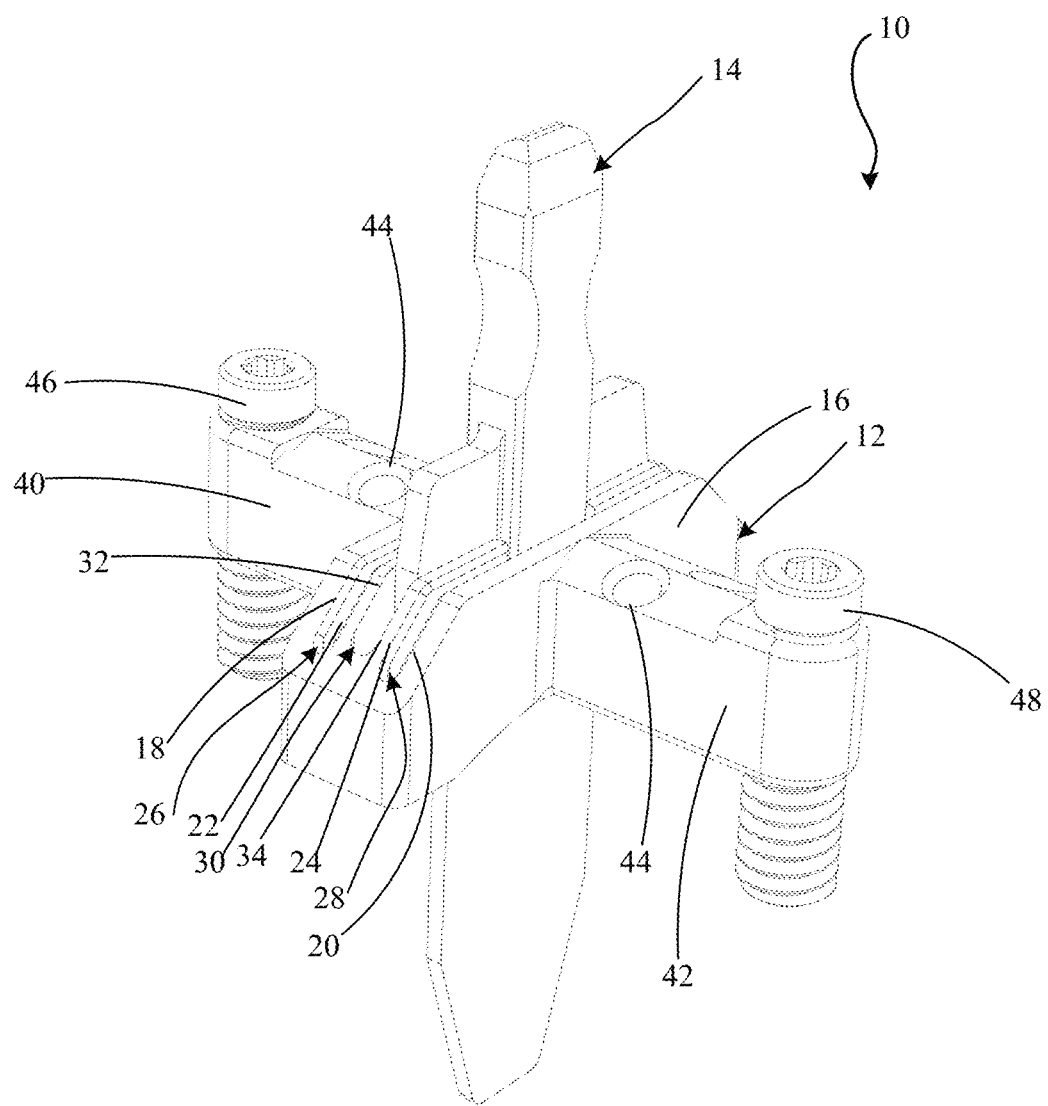
FIG. 1 is a perspective view of a bone preparing guide and spacer in accordance with an embodiment of the invention.

The details of one or more examples are set forth in the accompanying drawings and the description below. Other features, objects, and advantages will be apparent from the description and drawings, and from the claims.

DETAILED DESCRIPTION

The following detailed description is exemplary in nature and is not intended to limit the scope, applicability, or configuration of the invention in any way. Rather, the following description provides some practical illustrations for implementing exemplary embodiments of the present invention. Examples of constructions, materials, and dimensions are provided for selected elements, and all other elements employ that which is known to those of ordinary skill in the field of the invention. Those skilled in the art will recognize that many of the noted examples have a variety of suitable alternatives.

In general, this disclosure is directed to surgical instruments and techniques that can be used in a bone correction procedure. Embodiments of the disclosure include a spacer, bone preparing guide, and/or tissue removing instrument location check member along with methods of positioning such spacers and guides in a medical procedure. Such instruments can be used alone or in combination to improve the efficacy of a bone correction procedure as compared to when the procedure is used without the instruments.

In an exemplary application, embodiments of the spacer, bone preparing guide, and/or tissue removing instrument location check member can be used before and/or during a surgical procedure, such as a bone alignment, osteotomy, fusion procedure, and/or other procedures where one or more bones are to be prepared (e.g., cartilage or bone removal and/or cut). Such a procedure can be performed, for example, on bones (e.g., adjacent bones separated by a joint or different portions of a single bone) in the foot or hand, where bones are relatively smaller compared to bones in other parts of the human anatomy. In one example, a procedure utilizing one or more embodiments of the disclosure can be performed to correct an alignment between a metatarsal (e.g., a first metatarsal) and a second metatarsal and/or a cuneiform (e.g., a medial, or first, cuneiform), such as in a bunion correction surgery. An example of such a procedure is a Lapidus procedure (also known as a first tarsal-metatarsal fusion). In another example, the procedure can be performed by modifying an alignment of a metatarsal (e.g., a first metatarsal). An example of such a procedure is a basilar metatarsal osteotomy procedure.

For example, the described surgical instruments can be used in combination during a tarsometatarsal ("TMT") fusion procedure to achieve a multi-planar realignment (e.g., bi-planar, tri-planar) of a first metatarsal with respect to a medial cuneiform. The spacer can be used to properly position a bone preparation guide, or cut guide, with respect to the TMT joint and, more particularly, guide surfaces or slots of the cut guide with respect to bone ends to be cut. In some examples, one or more guide surfaces or slots of the cut guide are angled. For example, the cut guide may be configured to position a guide slot through which a cutting instrument is translated parallel to the end face of a first metatarsal while another guide slot is skewed with respect to the end face of a medial cuneiform. The guide slot positioned over the end of the medial cuneiform may angle proximally from the medial to the lateral sides of the medial cuneiform, resulting in a wedge-shaped section of bone being removed from the medial cuneiform. The disclosed instruments can help appropriately prepare the ends of the first metatarsal and medial cuneiform for repositioning in multiple planes (e.g., a frontal plane, a transverse plane, and/or a sagittal plane), allowing the first metatarsal to be corrected from an anatomically misaligned position to an anatomically aligned position.

FIG. 1 shows a perspective view of an exemplary bone preparing guide and spacer 10. The bone preparing guide and spacer 10 can include a bone preparing guide 12 and a spacer 14. In some applications, the bone preparing guide and spacer 10 can be provided to facilitate the positioning and/or preparation of a bone or bones. In the illustrated example, the bone preparing guide 12 includes a body 16 defining a first guide surface 18 to define a first preparing plane and a second guide surface 20 to define a second preparing plane. A tissue removing instrument (e.g., a saw, rotary bur, osteotome, etc., not shown) can be aligned with the guide surfaces to remove tissue (e.g., remove cartilage or bone and/or make cuts to bone). The first and second guide surfaces 18, 20 can be spaced from each other by a distance (e.g., between about 2 millimeters and about 10 millimeters, such as between about 4 and about 7 millimeters). In the embodiment shown, the first and second guide surfaces are parallel, such that cuts to adjacent bones using the guide surfaces will be generally parallel.

In some embodiments, as shown in FIG. 1, a first facing surface 22 is positioned adjacent the first guide surface 18 and/or a second facing surface 24 is positioned adjacent the second guide surface 20. In such embodiments, the distance between the first guide surface and the first facing surface defines a first guide slot 26, and the distance between the second guide surface and the second facing surface defines a second guide slot 28. Each slot 26, 28 can be sized to receive a tissue removing instrument to prepare the bone ends therethrough. The first and second slots 26, 28 may be parallel or skewed (e.g., non-parallel) to each other. In the illustrated embodiment, the facing surfaces each contain a gap along their respective lengths, such that each of the surfaces is not a single, continuous surface. In other embodiments, the facing surfaces can each be a single, continuous surface lacking any such gap.

In some embodiments, an opening 30 can be defined by the body 16 between the first and second facing surfaces 22, 24. The opening 30 can thus be an area between the slots 26, 28 useful, for instance, for allowing a practitioner to have a visual path to an osteotomy site (e.g., cartilage, bones, and/or joint space) during bone preparation and/or to receive instruments, as discussed further below. In the embodiment shown, the opening 30 extends across the body 16 a distance from a surface 32 opposite of the first facing surface 22 to a surface 34 opposite of the second facing surface 24.

The embodiment shown also includes a first end 40 extending from the body 16 in a first direction and a second end 42 extending from the body 16 in a second direction. The second direction can be different than the first direction (e.g., an opposite direction). The first and second ends 40, 42 can each extend out perpendicularly from the body 16 as shown or, in other embodiments, the first and second ends 40, 42 can extend out from the body at differing angles. As shown, each of the first end 40 and the second end 42 can include at least one fixation aperture 44 configured to receive a fixation device (e.g., a pin, not shown) to secure the guide 12 to one or more bones. Such apertures 44, as shown, may extend through each respective end at a vertical or skewed angle relative to a top surface of the guide 12.

The bone preparing guide 12 can also include a first adjustable stabilization member 46 engaged with the first end 40. In some embodiments, the bone preparing guide 12 also includes a second adjustable stabilization member 48 engaged with the second end 42. Each of the members 46, 48 can be threaded and engage a threaded aperture defined by the ends 40, 42. The elevation of each end 40, 42 can be adjusted with respect to one or more bones by adjusting the member 46, 48 at the end for which an elevation adjustment is desired. In some embodiments, as shown, the members 46, 48 may be cannulated such that they can receive respective fixation devices. While bone preparing guide 12 is illustrated with two adjustable stabilization members, in other examples, the guide can include fewer adjustable stabilization members (e.g., none, one) or more adjustable stabilization members (e.g., three, four, or more) and the disclosure is not limited in this respect.

As noted, the bone preparing guide as shown in FIG. 1 includes the spacer 14. The spacer can extend from the body in a third direction, the third direction being different than the first and second directions (e.g., perpendicular to the first and second directions), and it can be configured to be placed into a joint space between opposing bones. In some embodiments, the spacer is integral with the guide and the guide and spacer are a single component, for example, a unibody construction. In other embodiments, the spacer is physically separate from and insertable into the guide. In these embodiments, the spacer and bone cutting guide may be provided as part of a sterile kit (e.g., packed in single common container), alone or in combination with other components to facilitate the procedure being performed.

In the embodiment shown, the spacer 14 can be selectively engaged with the bone preparing guide 12, such that the spacer and guide can be attached and detached. For instance, the spacer 14 can be received by the body 16 of the guide 12, such as by inserting the spacer into opening 30. When the spacer 14 is received in the opening 30, the spacer 14 may extend from the body in between the first guide surface 18 and the second guide surface 20, or in between the first and second slots 26, 28, when provided. In some instances where the spacer 14 is received within the opening 30, no connection between the guide 12 and spacer 14 need be present, as the opening 30 itself may be sufficient for engaging the guide and spacer. The spacer 14 can engage the guide 12 such that the guide 12 and/or spacer 14 can move relative to one another while engaged (e.g., in a vertical direction). For example, in some embodiments, the guide 12 can move relative to the spacer 14 while the guide 12 and spacer 14 are engaged, such that the guide can be inserted over the spacer or removed from the spacer while the spacer is engaged within a joint space. For example, a distal portion of the spacer can be inserted into a joint space (e.g., tarsal-metatarsal joint space) and the guide 12 positioned over the top of the spacer with a proximal portion of the spacer projecting out from the top of the guide. In yet further embodiments, the guide 12 and spacer 14 can be removably attachable, such as by magnets, a snap-fit, male-female interfacing parts, or other temporary connections.

Figure 2A:
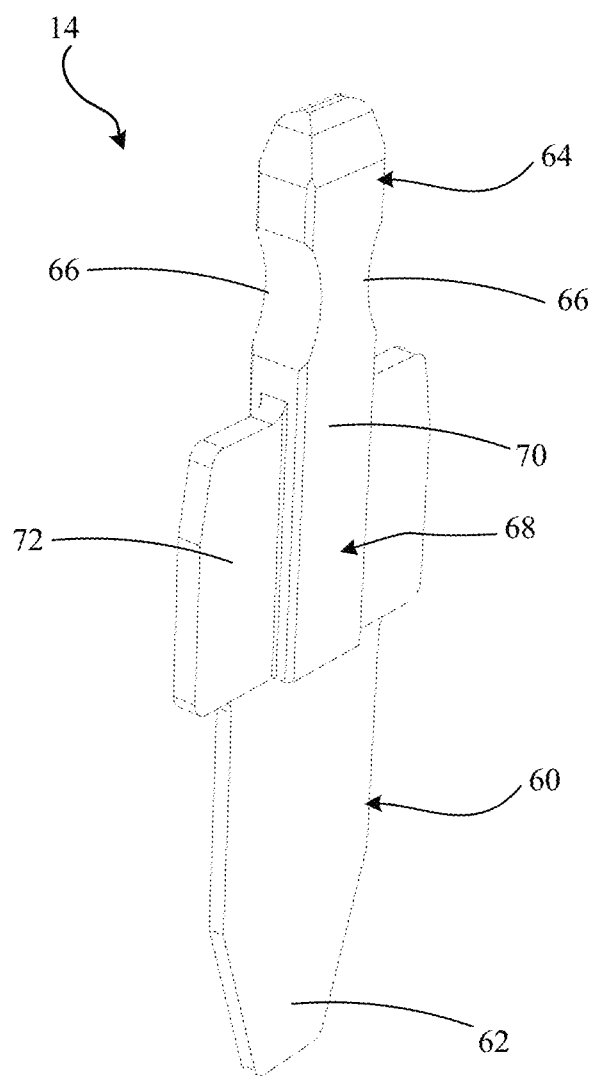
FIG. 2A is a perspective view of a spacer in accordance with an embodiment of the invention.
Figure 2B:
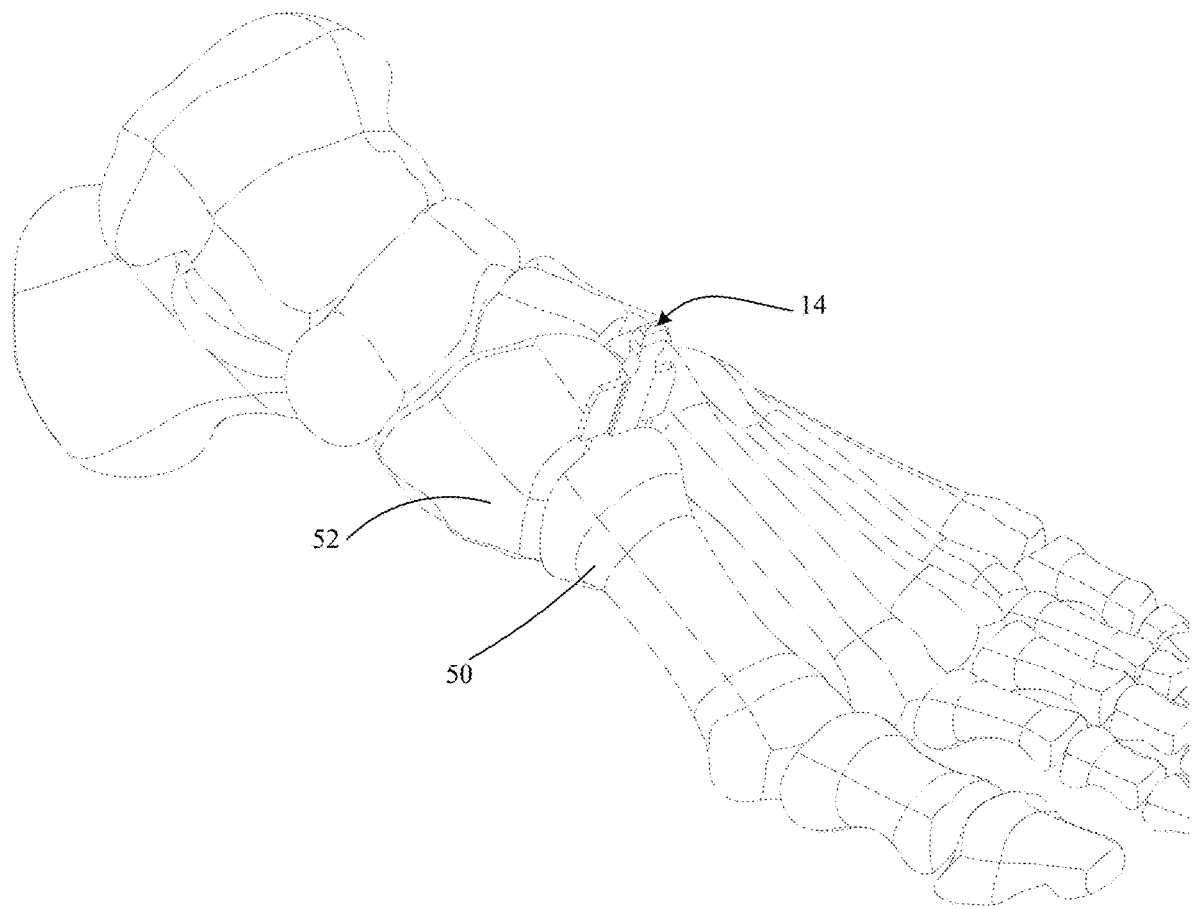
FIG. 2B is a perspective view of the spacer of FIG. 2A on a foot in accordance with an embodiment of the invention.

FIGS. 2A and 2B show an embodiment of a spacer 14. In some embodiments, the spacer 14 is configured to be used to guide bone preparation instruments during a surgical procedure. In other embodiments, the spacer 14 is configured to be inserted into a bone preparation guide. FIG. 2A illustrates a perspective view of the spacer 14, while FIG. 2B illustrates the spacer 14 on a foot. The spacer 14, whether a stand-alone component, a separate component selectively engageable with a guide, or integrated with a guide, can be configured to be inserted into a space between two bones 50 and 52 (e.g., adjacent bones separated by a joint or different portions of a single bone).

In one application, the space between two bones into which the spacer 14 is configured to be inserted can be a TMT joint space, such as the first metatarsal-cuneiform joint as shown in FIG. 2B where bone 50 is a first metatarsal and bone 52 is a medial cuneiform. The spacer 14 can be inserted into a space between two bones in a variety of differing directions, depending on the application. In one example, the spacer 14 is inserted from the generally dorsal side of a foot. In another example, the spacer 14 is inserted from a generally dorsal-medial side of a foot or a medial surface of a foot.

As seen in the embodiment of FIG. 2A, the spacer 14 can include a first portion 60 that is configured to extend, at least partially, into a space between two bones (e.g., a joint space between bones 50 and 52 as shown in FIG. 2B). In the embodiment shown in FIG. 2A, the first portion 60 is a generally planar member having opposite planar surfaces. In other embodiments, the generally planar member has one or more slots and/or apertures. In yet other embodiments, the first portion has at least two extending members configured to extend into the joint space. The extending members can include any cross-sectional shape, such as cylindrical, triangular, or frustoconical shape.

As shown in FIG. 2A, the first portion 60 can include a keel 62, where the keel 62 is configured to facilitate insertion of an end of the first portion 60 into the space between two bones. As shown, the tip of the keel 62 is linear (e.g., extending in a plane parallel to the width of the keel). In other embodiments, the tip of the keel 62 may be rounded and/or tapered to provide for easier insertion of the keel 62 into the space between two bones. In some embodiments, the keel 62 can have a width that is less than or equal to a width of the space between two bones (e.g., a width of a joint). In addition, the keel 62 can have a thickness (e.g., extending in a direction perpendicular to the width of the keel and along the length of the space between two bones) that is equal to or less than the length of the space between two bones. In certain applications it may be desirable to configure the thickness of the keel 62 to be thicker relative to the length of the space between two bones such that the keel 62 fits snuggly into the space between two bones. For example, the thickness of the keel 62 may be sized to alter, such as expand, the space between two bones when inserted. The keel 62 can have a uniform thickness along its length as seen in FIG. 2A or can have a thickness that varies, such as a thickness that tapers in a direction proceeding toward the tip of the keel 62 (e.g., a wedge-shaped keel).

A length of the keel 62, and first portion 60, can be configured to allow the keel 62 to extend vertically to a bottom base of the space between two bones (e.g., where the spacer 14 is used in an application on the foot as seen in FIG. 2B, the keel 62 can extend from a generally dorsal side of the foot to a generally plantar side). In other examples, the length of the keel 62 can be configured such that the keel 62 extends only partially into the space between two bones, such as through a point in the space between two bones where there is present opposing interfacing surfaces (e.g., planar interfacing surfaces of two bones) and stops extending into the space between two bones where a bump or eccentric interfacing surface is present. The keel 62 as shown in the illustrated example is generally linear along its length. However, in other examples the keel 62 may include one or more contours along its length, where the one or more contours are configured to conform to an anatomic geometry of one or more bone ends interfacing at the space into which the keel 62 is inserted.

The keel 62, and the first portion 60, can be made of various materials appropriate for one or more desired applications of the spacer. In one example, the keel can made of a rigid material, such as metal or plastic, which does not deform or otherwise change geometry when inserted into the space between two bones. By preventing the keel from deforming when inserted into the space between two bones, the spacer can be maintained in general alignment with the interfacing bone surfaces at the space. In other examples, the keel can be made of a flexible material in order to generally maintain alignment of the spacer with the interfacing bones surfaces at the space while providing the keel with some give in its geometry to conform to one or more non-parallel portions of interfacing bones at the space. In other embodiments, the keel includes a combination of a rigid material and a flexible material. For example, a perimeter of the keel may include the flexible material to facilitate insertion into the joint space and a central portion can include a rigid material to prevent deformation.

The spacer 14 can further include a second portion 64 at or near an end of the spacer 14 opposite the keel 62. The second portion 64 can be designed to be gripped, such as by a hand of a surgeon during a procedure. The second portion 64 can have, in some instances, one or more recesses 66 (two recesses 66 are shown in FIG. 2A, with each recess 66 disposed opposite the other) to enhance a grip on the second portion 64. In some embodiments, the second portion 64 can also include a roughened texture to also enhance a grip on the second portion 64. The one or more recesses 66 and/or roughened texture can be particularly beneficial where the second portion 64 is to be gripped by a wet and/or gloved hand of a surgeon.

In some embodiments, the spacer 14 can have an intermediate portion 68 disposed between the first and second portions 60, 64. The first, second, and intermediate portions can be provided as an integral member or can be provided as separately joined components. In either case, each portion can comprise a material different from the other portions, and the material can have different characteristics, such as rigidity and flexibility, than the materials of the other portions. Alternatively, all the portions of spacer 14 may be fabricated from the same material, such as a unitary body formed of metal or plastic.

In embodiments where the spacer is provided as a separate component from the bone preparation guide and configured to be engaged with the bone preparation guide, the intermediate portion 68 can be engageable with the body of the guide (e.g., at the opening defined by the body of the guide). In the example shown, the intermediate portion 68 can have a first region 70 and a second region 72. The first region 70 can have an extended thickness relative to the thickness of the first portion 60 (and thus the keel 62) and can transition from interfacing with the guide to the second portion 64 along its length. The second region 72 can have an extended width relative to the width of the first portion 60 (and thus keel 62). The extended thickness of the first region and/or the extended width of the second region 72 can allow the spacer 14 to be more stably received by the body of the guide in examples where the spacer 14 and guide are separate components.

In embodiments where the spacer 14 is configured to be used as a stand-alone device without a bone guide, the intermediate portion 68 can be used to provide a first guide surface and an opposite second guide surface. In such embodiments, the first portion 60 (and thus the keel 62) of the spacer can be inserted into a joint space, and a surface of the intermediate portion 68 can be used to provide a guide surface. For example, the surface of the first region 70 on a first side of the spacer 14 can be configured as a first guide surface, and the surface of the first region 70 on an opposite side of the spacer 14 can be configured as a second guide surface. In some embodiments, at least the first region 70 of the intermediate portion 68 has a thickness greater than the thickness of the first portion 60. The difference in thickness of the first region 70 and the first portion 60 on each side of the spacer 14 can define a length and thickness of tissue to be removed by a tissue removing instrument guided by the surface of the intermediate portion.

In use, the first portion 60 may be inserted into a joint space and a tissue removal instrument placed against the intermediate portion 68 to guide a preparation of a first bone on a first side of the spacer 14. A tissue removal instrument can be placed against the intermediate portion 68 to guide a second preparation to a second bone on a second, opposite side of the spacer 14. In a specific example, the tissue removing instrument can be guided by the spacer 14 for about one-half of a thickness of the tissue to be removed. Then the spacer can be removed from the joint space and the tissue removing instrument could be reinserted to finish the tissue removal.

Figure 3A:
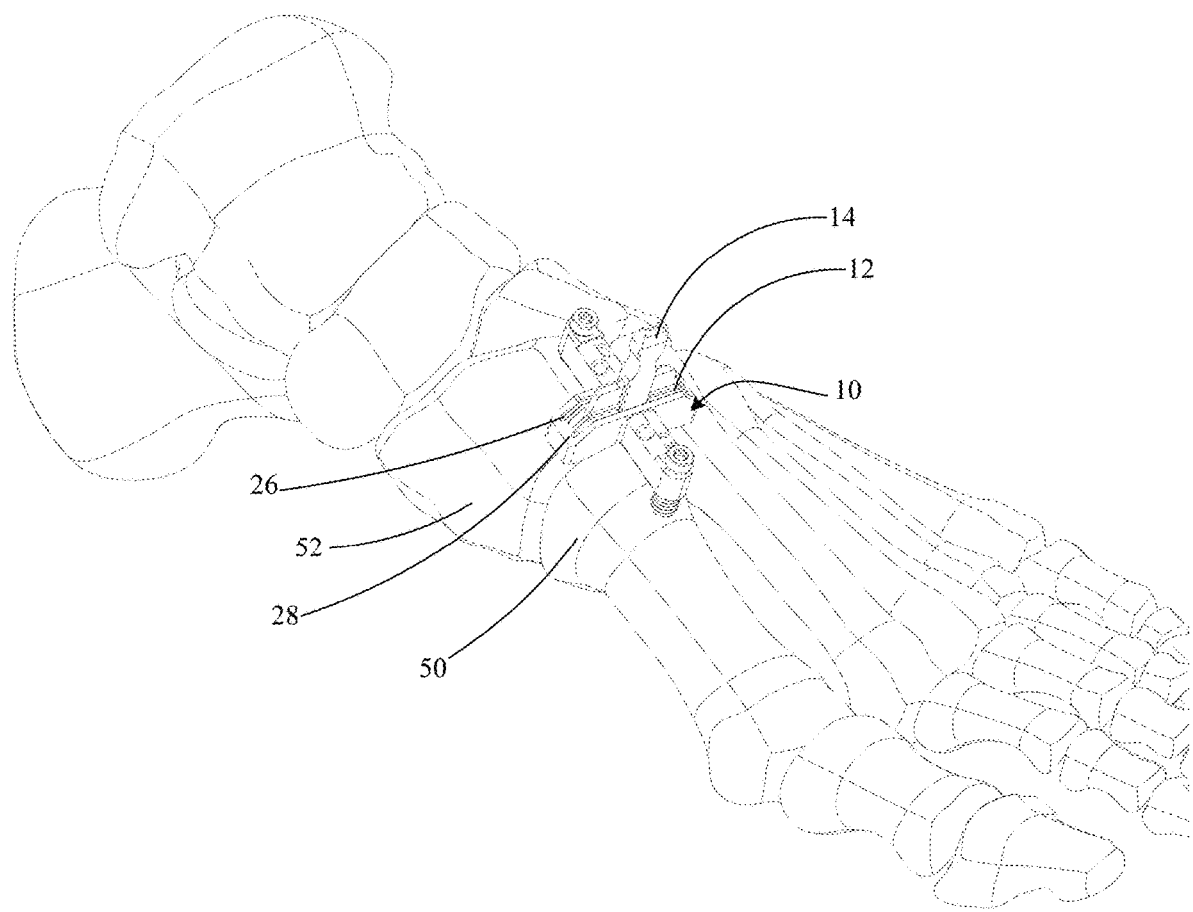
FIGS. 3A and 3B are perspective and side views, respectively, of the bone preparing guide and spacer on a foot in accordance with an embodiment of the invention.
Figure 3B:
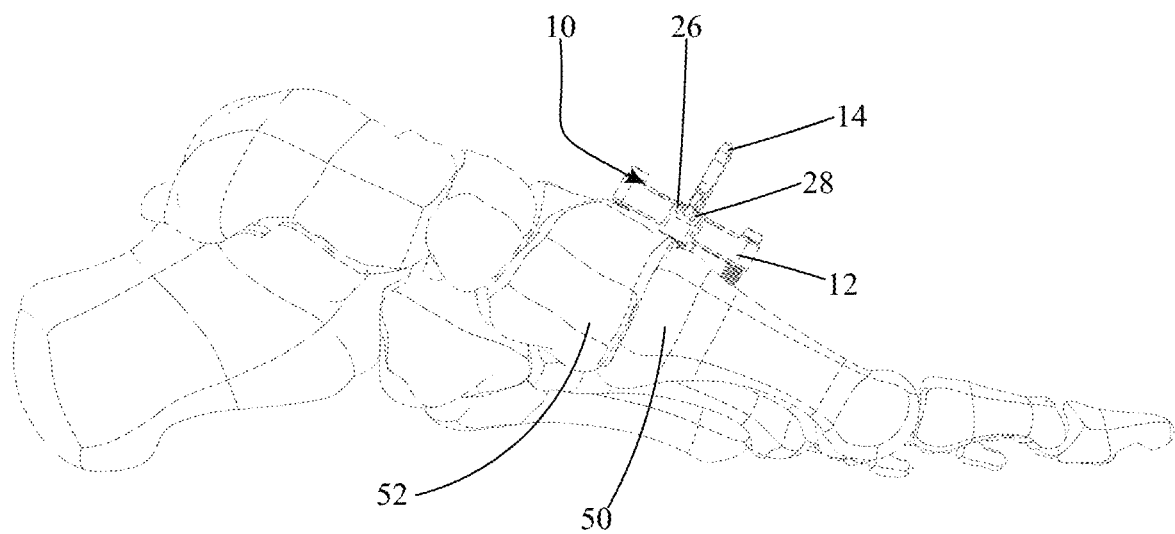

FIGS. 3A and 3B show perspective and side views, respectively, of the bone preparation guide and spacer 10 on a foot. Depending on the embodiment, the bone preparing guide and spacer 10 can be positioned onto the foot in different ways. In embodiments where the spacer 14 is a separate component from the guide and configured to be engaged with the guide, the spacer 14 can first be inserted into the space between two bones (as shown in FIG. 2B). In such embodiments, after the spacer 14 is appropriately inserted into the space between two bones, the guide 12 can then be placed onto the foot so as to engage the already inserted spacer 14 (e.g., by sliding the guide 12 vertically downward toward the foot on the spacer 14, such as via the opening defined by the body of the guide 12). Alternatively, the guide 12 can first be positioned in proximity to the space between two bones and the spacer 14 then inserted through the guide 12 and into the joint space underlying the guide. The guide 12 can preliminarily position the spacer 14 (e.g. via the opening defined by the body of the guide 12) into the space between two bones. After preliminarily being positioned, the clinician can manipulate the location of guide 12 and/or spacer 14 to orient the components at a desired location relative to the two bones (e.g., by orienting the cutting slots of the guide 12 relative to the ends of bones 50 and 52, respectively). In other embodiments (e.g., where the spacer 14 and guide 12 are integral or separate components), the bone preparing guide and spacer 10 can be positioned on the foot with guide 12 being positioned in the joint between the two bones as a single structure, e.g., thereby simultaneously positioning the guide 12 and spacer 14 on the foot.

Independent of how spacer 14 is inserted into the joint between bones 50, 52 relative to installation of guide 12 over the bones, the spacer 14 can serve to provide initial stability to the guide 12 (e.g., prior to the guide 12 receiving fixation devices). For example, the spacer 14 can engage with the guide 12 and, once seated in the space between the bones, act to support the guide 12. Moreover, where the guide 12 and spacer 14 are separate components insertable into each other, the depth that the spacer 14 is inserted within the space between bones can be adjusted without needing to remove the guide 12. Similarly, the distance between where the guide 12 is positioned vertically in relation to the space between bones can be adjusted while leaving the spacer 14 in place.

In operation, spacer 14 can serve as an alignment and/or reference tool for the guide 12 with respect to the one or more bone surfaces to be prepared (e.g., cut, morselized). Such surfaces to be prepared can include all or a portion of an interfacing surface of bone 50 or 52 as shown. When the spacer 14 is inserted into the space (e.g., a joint) between the bones 50, 52, the spacer 14 can act to align the guide 12 at an appropriate position (e.g., longitudinal along the bones 50, 52) and orientation (e.g., angle relative to the bones 50, 52 in multiple planes selected from more than one of a frontal plane, a transverse plane, and a sagittal plane) for the intended procedure relative to the surfaces of the bones 50, 52 to be prepared.

For example, when the spacer 14 is inserted into the space between bones 50, 52, the spacer can help align and orient, in one or more planes, the first guide surface 18 and the second guide surface 20 (and/or slots 26, 28, when provided) of the guide 12 relative to respective surfaces of the bones 50, 52 to be prepared. When inserted into the space between bones 50, 52, the spacer 14 can engage the guide 12 (e.g., physically restrict the free range of movement of guide 12), longitudinally aligning the guide 12 with the surface of each of bones 50 and 52 to be prepared. For example, spacer 14 can longitudinally align the first guide surface 18 with the end surface of the bone 52 and the second guide surface 20 with the end surface of the bone 50. Additionally, when inserted into the space between bones, the spacer 14 can extend out from the space and provide an indication as to the location of the interfacing, end surfaces of each of bones 50 and 52. In this way, orienting the guide 12 relative to the spacer 14 serves as an angular reference relative to the end surfaces of each of bones 50 and 52. Thus, the spacer 14 can facilitate accurate preparation of a desired surface of one or more bones 50, 52.

In some applications, it can be desirable to prepare interfacing surfaces of one or both bones 50, 52 by cutting a slice from one or both surfaces, where the slice has a generally constant thickness. In such an application, the spacer 14 can be configured to orient a first guide surface 18 parallel to the preparation surface of bone 52 and/or a second guide surface 20 parallel to the preparation surface of bone 50. In the case of a metatarsal-cuneiform joint as shown in FIG. 3A, where interfacing bone end surfaces are relatively planar, orienting the first guide surface 18 and the second guide surface 20, or slots 26, 28, when provided, parallel to the bone end surfaces to be cut using the spacer 14 as a reference can facilitate removal of a slice of relatively constant thickness. Depending on the procedure being performed, the end of bone 50 facing bone 52 and/or the end of bone 52 facing bone 50 may be morselized in addition to or in lieu of being cut to prepare the end of the bone.

In other additional or alternative applications, it can be desirable to prepare interfacing surfaces of one or both bones 50, 52 by cutting a wedge-shaped portion from the interfacing surfaces of one or both bones 50, 52, where the wedge-shaped portion does not have a uniform thickness (e.g., in the medial to lateral direction of cut). For instance, in one application, a plantar-based wedge may be cut from a medial cuneiform (e.g., bone 52), e.g., to correct a misaligned first metatarsal (e.g., bone 50). To cut a wedge-shaped portion from the interfacing end surface of one or both bones 50, 52, the first guide surface 18 and the second guide surface 20, or slots 26 and 28, when provided, can be oriented at a skewed angle relative to respective bones 52 and/or 50 using the spacer 14 as a reference for the skewed angle at which the one or more bones 50, 52 are to be cut. For example, first guide surface 18 and/or second guide surface 20 may skew proximally back along the length of the medial cuneiform as the guide surface extends from the medial side of the medial cuneiform to the lateral side of the medial cuneiform. As a result, the bone portion cut using a guide surface so configured can remove more bone from the lateral side of the medial cuneiform than the medial side of the medial cuneiform, resulting in a wedge-shaped portion of bone being removed from the medial cuneiform.

In addition to serving as a reference for positioning and orientation in bone preparation, the spacer 14 can also serve as a reference for indicating a thickness of tissue (e.g., such as bone) to be removed from a surface of a bone 50 and/or 52. For instance, a distance between a first longitudinal surface of spacer 14 and the first guide surface 18 may define a thickness of tissue to be cut from the surface of the bone 52. Similarly, a distance between a second longitudinal surface (e.g., opposite the first longitudinal surface) of the spacer 14 and the second guide surface 20 may define a thickness of tissue to be cut from the surface of the bone 50. Thus, a clinician can utilize the spacer 14 as a reference prior to preparing one or more bones in order to visualize whether the proposed bone preparation matches the desired bone preparation, such as whether the thickness of the cut to be made is in accordance with a desired thickness of tissue to be removed, and make any adjustments prior to implementation of the bone preparation action.

In some embodiments, a guide can be designated with an identification number representing a cut thickness facilitated by that particular guide, which is defined by the distance between an adjacent surface of the spacer 14 and the respective guide surface of the guide. In certain embodiments, the distance between a first guide surface 18 and the spacer 14 can be different from the distance between a second guide surface 20 and the spacer 14, such that different thickness cuts can be made on different, interfacing bones. In some examples, the distance between one or more guide surfaces on the guide and the spacer 14 can be adjustable, allowing a user to vary the thickness of matter removed by a cut.

In applications where cut guide 12 includes a guide surface (e.g., first guide surface 18 and/or second guide surface 20) that skews proximally from the medial to the lateral side of the foot to which the cut guide is applied, the angle of skew may be fixed or may be variable. For example, cut guide 12 may have an adjustable guide surface (e.g., first guide surface 18 and/or second guide surface 20) where the angle of skew can be adjusted. In practice, a clinician can set the angle of the guide surface(s) relative to the bone, e.g., to remove more on the lateral side than the medial side, more on the medial side than the lateral side, or the same amount on both the lateral and medial sides, depending on the angle set. In some configurations, the adjustable angle can be temporarily fixed, or locked, to prevent inadvertent movement after setting the desired angle. Depending on the design, the guide surface (e.g., first guide surface 18 and/or second guide surface 20) may be adjustable to provide an angle (e.g., between the guide surface and first and/or second facing surfaces 22, 24) ranging from 0 degrees to 25 degrees, such as 0 degrees to 10 degrees. For example, the guide surface may be adjustable from 25 degrees to a non-zero degree angle less than 25 degrees.

Although the spacer 14 is illustrated to be engageable with the guide 12, the spacer 14 can also be configured to engage with other guides. For example, spacer 14 may be used as part of a kit that includes a plurality of guides with different sized cut widths. A clinician can select one of the plurality of different sized guides and use the selected guide in combination with the spacer to perform a procedure. For example, a clinician may select one guide 12 to engage with spacer 14 and provide a designated first cut thickness. If the clinician, using the spacer 14 as a reference, determines that the cut thickness that would result using the first guide is not desirable for the particular operation, the spacer 14 can be removed from the first guide and engaged with a second guide having a designated second cut thickness different from the first cut thickness of the first guide.

While spacer 14 illustrated and described above with respect to FIGS. 1-3 can provide an effective tool for performing various medical procedures, such as helping to position a bone preparation guide during a tarsal-metatarsal fusion procedure, the configuration of spacer 14 may vary, e.g., depending on the characteristics of use and targeted clinical outcome.

As one example, the width of the spacer 14 can be sized such that the spacer extends into a lateral region of adjacent bone ends, when the spacer is positioned between the bones. For example, the width of the portion of spacer 14 configured to be positioned between adjacent portions of bone (e.g., first portion 60) can be wide enough (in the medial to lateral direction) that the spacer extends at least into the lateral half of the end faces of the adjacent bones between which the spacer is positioned.

For example, when spacer 14 is configured to be inserted into a tarsal-metatarsal joint space (e.g., between first metatarsal 50 and medial cuneiform 52), first portion 60 of the spacer may be project laterally a distance sufficient to position the first portion of the spacer between the lateral half of the end faces of first metatarsal 50 and medial cuneiform 52. The first portion 60 may contact the ends of first metatarsal 50 and medial cuneiform 52 on the lateral side of the bone ends (e.g., lateral-most half, lateral-most third, lateral-most edges). In some configurations, the first portion 60 of spacer 14 extends laterally a distance sufficient to contact a medial side of an adjacent bone (e.g., second metatarsal), when positioned between first metatarsal 50 and medial cuneiform 52.

In configurations where spacer 14 is symmetric, the first portion 60 of the spacer may also project medially to contact the ends of first metatarsal 50 and medial cuneiform 52 on the medial side of the bone ends (e.g., medial-most half, medial-most third, medial-most edges). Alternatively, as discussed in more detail below, first portion 60 may be laterally offset in the medial-lateral dimension. In either case, second portion 64 may be symmetric with respect to the first portion and have the same width as the first portion or may be asymmetric with respect to the first portion and/or have a different width than the first portion.

Configuring spacer 14 to have a portion positionable within a lateral portion of a joint space can be useful to help prevent misalignment of guide 12. In practice, when bone 50 is realigned relative to bone 52 and/or an adjacent bone (e.g., second metatarsal), a gap between bone 50 and bone 52 may open on the medial side of the joint space between the ends of the bones. This gap may occur, e.g., as an intermetatarsal angle between a first metatarsal and second metatarsal is closed by pivoting and/or rotating the first metatarsal toward the second metatarsal. In some situations, as a gap on the medial side of the joint space opens, a spacer positioned inside of the joint space can shift (e.g., laterally or medially) and/or rotate (e.g., such that the portion of the spacer above the joint space does not project dorsally but instead projects in a lateral-dorsal or medial-dorsal direction). When the guide 12 is subsequently positioned over the shifted and/or rotated spacer 14, the cutting surface(s) of the guide may be misaligned with respect to when the ends of bones 50 and 52 are desirably cut.

By configuring the spacer 14 so that at least a portion of the spacer positioned between the ends of bones 50 and 52 (e.g., within the tarsal-metatarsal joint space) is on the lateral side of the joint space, the spacer may remain properly positioned through realignment of bone 50. For example, as the intermetatarsal angle between a first metatarsal and second metatarsal is closed by pivoting and/or rotating the first metatarsal toward the second metatarsal, the lateral side of the ends of bones 50 and 52 may move toward each other while the medial side of the ends of the bones may move away from each other. This can pinch the lateral portion of spacer 14 between the ends of the bones (e.g., by having the lateral sides of the ends of the bones press against opposing sides of the spacer). As a result, the spacer 14 may be retained in a stable position in the joint space between the bones such that, when guide 12 is subsequently positioned over spacer 14, the guide is appropriately positioned to cut the ends of bones 50 and 52 (e.g., by translating a cutting instrument along and/or through guide surfaces of the guide to resects the bone ends).

Spacer 14 can have a variety of different configurations that allow at least a portion of the spacer to be positioned on lateral sides of the end faces of the bones between which the spacer is inserted. As another example, the portion of spacer 14 that is configured to project plantarly of bone preparation guide 12 (e.g., the portion positioned in the joint space between opposed ends of bones 50 and 52 while guide 12 is positioned on top of the bones) may be asymmetrical with respect to portion of the spacer located inside of guide 12 and/or projecting out of the top of the guide (e.g., dorsally of the guide). For example, instead of configuring first portion 60 of spacer 14 to be positioned substantially centered in the joint between the ends of bones 50 and 52, the first portion 60 of the spacer may be offset relative to an axis extending through a geometric center of the ends of the bones and the joint therebetween. When so configured, the spacer 14 may be inserted into one side of the joint space between the bones 50 and 52 while leaving another side of the joint space devoid of any spacer substrate.

As one example in accordance with this configuration, spacer 14 may be configured so that first portion 60 is offset relative to an axis extending through a geometric center of second portion 64. For example, when second portion is configured to have guide 12 insertable into and removable over the top of the second portion 64, first portion 60 may project downwardly from one side of the second portion. In use, such a configuration can cause first portion 60 to project asymmetrically with respect to the cross-sectional plane (e.g., medial-lateral plane at a single elevation) relative to second portion 64 and/or guide 12 positioned over the guide.

For example, when spacer 14 is configured to be inserted into a tarsal-metatarsal joint space (e.g., between a first metatarsal and medial cuneiform), first portion 60 of the spacer may be laterally offset relative to second portion 64. That is, first portion 60 may be positioned preferentially toward the lateral side of the joint as opposed to the medial side of the joint. The laterally-offset first portion 60 of spacer 14 may contact the ends of bones 50 and 52 on the lateral side of the bone ends (e.g., lateral-most half, lateral-most third, lateral-most edges) but not on the medial side of the bone ends (e.g., medial-most half, medial-most third, medial-most edges). The second portion 64 of the spacer may be substantially centered between the lateral and medial edges of bones 50 and 52. Accordingly, the portion of spacer 14 that is visible by the clinician and/or used to orient guide 12 (e.g., by positioning the guide over the spacer) can be substantially centered in the medial-lateral direction over the ends of the bones 50 and 52. However, the portion of spacer 14 that actually projects below the dorsal face of bones 50 and 52 in the plantar direction can be offset to the lateral side in the medial-lateral direction.

Figure 4A:
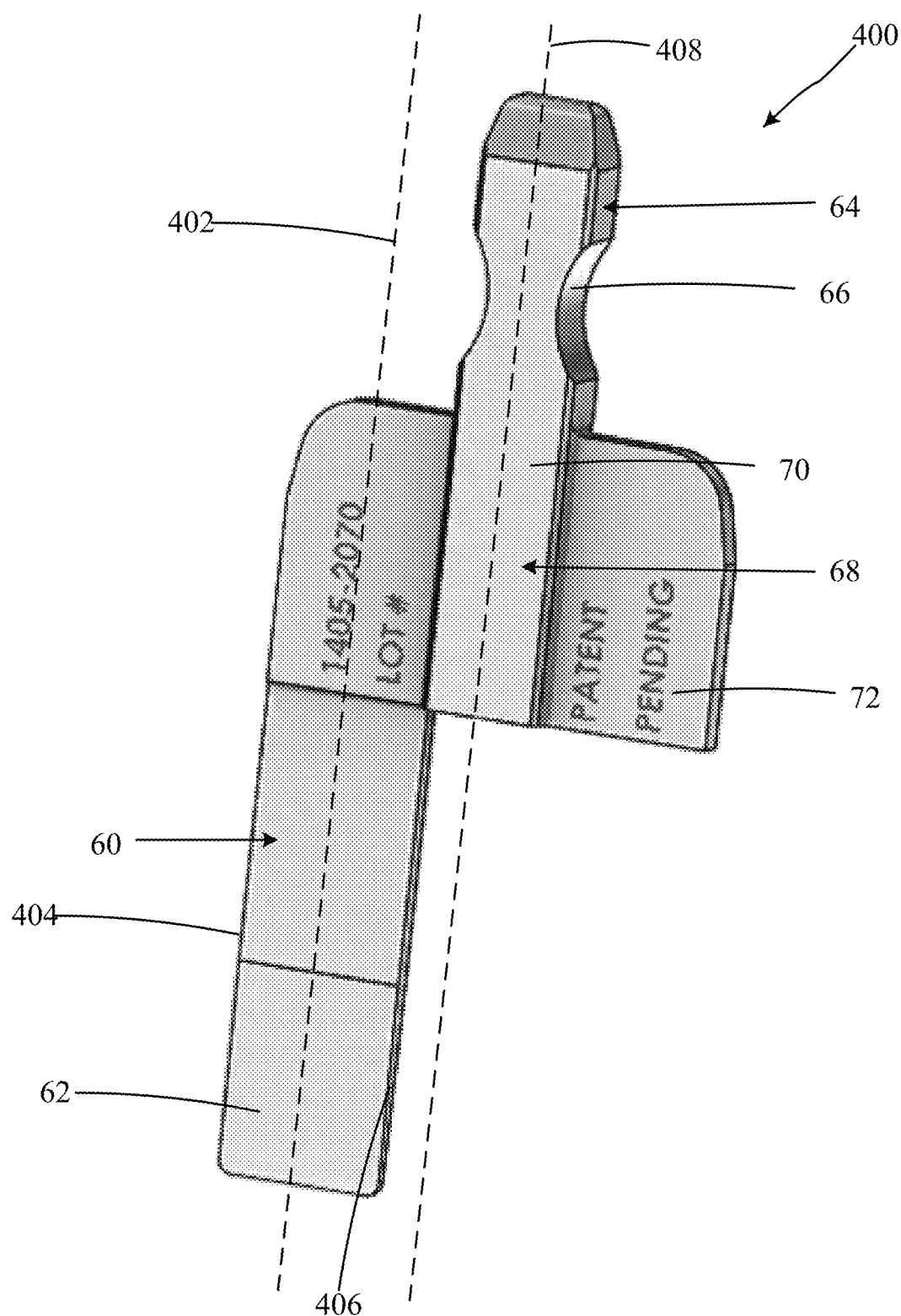
FIG. 4A is a perspective view of a spacer in accordance with another embodiment of the invention.
Figure 4B:
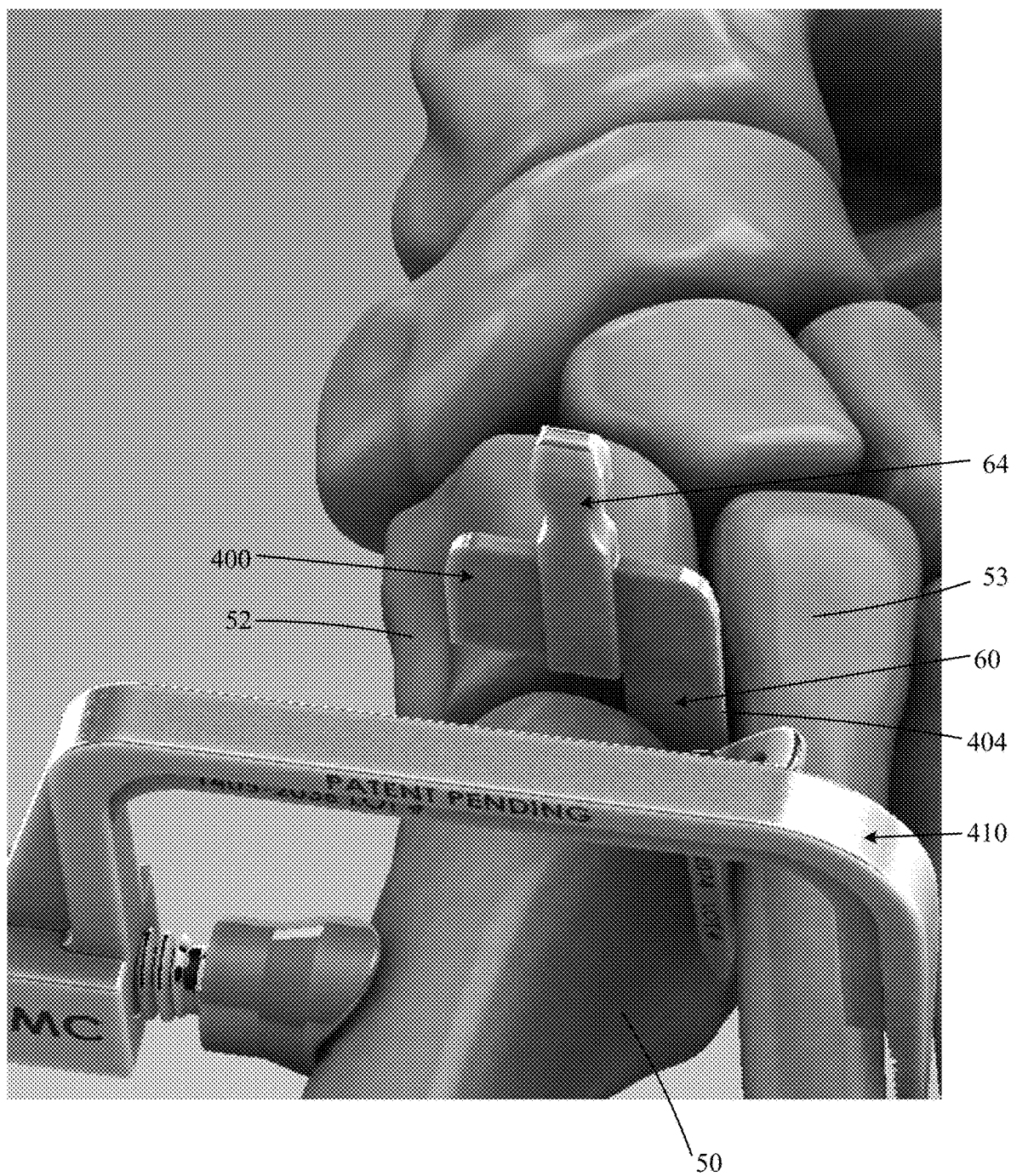
FIG. 4B is a perspective view of the spacer of FIG. 4A on a foot in accordance with an embodiment of the invention.

FIGS. 4A and 4B illustrate an example configuration of a spacer 400 that has a laterally offset structure positionable within a joint space. FIG. 4A illustrates a perspective view of the spacer 400, while FIG. 4B illustrates a perspective view of the spacer 400 on a foot. Like reference numerals used with respect to spacer 400 refer to like elements discussed above with respect to the spacer 14. The spacer 400, whether a stand-alone component, a separate component selectively engageable with a guide, or integrated with a guide, can be configured to be inserted into a space between two bones 50 and 52 (e.g., adjacent bones separated by a joint or different portions of a single bone). In one application, the space between two bones into which the spacer 400 is configured to be inserted can be a tarsometatarsal ("TMT") joint space, such as the first metatarsal-cuneiform joint as shown in FIG. 4B.

As shown in the example of FIG. 4A, the spacer 400 includes the first portion 60 that is configured to extend, at least partially, into a space between two bones (e.g., a joint space between bones 50 and 52 as shown in FIG. 4B). The first portion 60 defines a central longitudinal axis 402. The first portion 60 further includes a first sidewall 404 and a second sidewall 406 defining a width of the first portion 60 therebetween. The first portion 60 can include a keel 62, where the keel 62 is configured to facilitate insertion of an end of the first portion 60 into the space between two bones. In one example, a thickness of the keel 62 can taper moving in a direction toward the tip of the first portion 60 (e.g., toward the tip of the keel 62). In some cases, the keel 62 can extend vertically to a bottom base of the space between two bones, and in other cases the keel 62 may only partially extend into the space between two bones. Independent of whether the thickness of first portion 60 (including keel 62) is constant across the length of the first portion or varies, in some examples, the thickness ranges from 0.2 mm to 3 mm, such as from 0.38 mm to 1.8 mm.

The spacer 400 illustrated in FIGS. 4A and 4B further includes a second portion 64 at or adjacent an end of the spacer 400 opposite the keel 62. As seen in FIG. 4A, the second portion 64 has a central longitudinal axis 408. The second portion 64 can be designed to be gripped, such as by a hand of a surgeon during a procedure. The second portion 64 can have, in some instances, one or more recesses 66 and/or a roughened texture to enhance a grip on the second portion 64.

The spacer 400 can also have, in some embodiments, an intermediate portion 68 disposed between the first and second portions 62, 64. In embodiments where the spacer 400 is provided as a separate component from the bone preparation guide and configured to be engaged with the bone preparation guide, the intermediate portion 68 can be engageable with the body of the guide (e.g., at the opening defined by the body of the guide). In the example shown, the intermediate portion 68 has a first region 70 and a second region 72. The first region 70 can have an extended thickness relative to the thickness of the first portion 60 (and thus the keel 62) and can transition from interfacing with the guide to the second portion 64 along its length. The second region 72 can have an extended width relative to the width of the first portion 60 (and thus keel 62). In the example shown, the intermediate portion 68, including the first and second regions 70, 72, has a central longitudinal axis that coincides (e.g., is coaxial) with the central longitudinal axis 408 of the second portion 64.

As shown in FIGS. 4A and 4B, the embodiment of spacer 400 illustrated has a generally offset configuration. In some examples, an offset configuration of the spacer 400 includes the first portion 60 being offset from the second portion 64 and/or the intermediate portion 68. In the illustrated embodiment, where the second portion 64 and the intermediate portion 68 have the central longitudinal axis 408 in common, the first portion 60 is offset from both the second portion 64 and the intermediate portion 68. In particular, the central longitudinal axis 402 of the first portion 60 is spaced from the central longitudinal axis 408 of the second portion 64 and intermediate portion 68. While the specific dimensions can vary depending on the desired application, in some configurations, the distance separating a geometric enter of the central longitudinal axis 402 of the first portion 60 from the geometric center of the central longitudinal axis 408 of the second portion ranges from 1 mm to 20 mm, such as from 3 mm to 17 mm. While the width of first portion 60 (from first sidewall 404 to second sidewall 406) may also vary, in some instances, the width ranges from 2 m to 25 mm, such as 5 mm and 20 mm. Accordingly, in some configurations, a distance from a geometric center of central longitudinal axis 408 to first sidewall 404 bounding the lateral-most extend of spacer 14 may range from 5 mm to 15.

The spacer 400 can be inserted into the space between two bones 50 and 52, such as shown in FIG. 4B. When inserted, the offset configuration of the spacer 400 can result in the first portion 60 contacting the bones 50 and 52 (e.g., the end faces of the bones) and optionally an adjacent third bone 53 (e.g., a medial side of the bone), while the second portion 64 and central longitudinal axis 408 thereof is generally positioned at a center of the joint. In the illustrative example of FIG. 4B, the spacer 400 is inserted into the first TMT joint and the first portion 60 contacts the first metatarsal 50, first cuneiform 52, and second metatarsal 53. For instance, a first face surface of the first portion 60 can contact the first metatarsal 50, a second face surface of the first portion 60 opposite the first face surface can contact the first cuneiform 52, and the first sidewall 404 of the first portion 60 can contact the medial side of the second metatarsal 53. Thus, while the central longitudinal axis 408 of the second portion 64 may be generally centered between a medial side and a lateral side of the TMT joint, the central longitudinal axis 402 of the first portion 60 may be generally closer to the lateral side than the medial side of the TMT joint (e.g., at a lateral third of the TMT joint). Accordingly, in some instances, the first portion 60 may be inserted and secured within only a lateral region of the TMT joint.

The offset configuration of the spacer 400 can be useful in providing a stable spacer within the joint space, for instance, during a procedure where a bone alignment is to be altered. For example, in one type of bone alignment procedure the bone 50 may need to be realigned (e.g., using positioner device 410) in a manner that reduces an angle between the bone 50 and the bone 53. While the bone 50 is realigned, a gap at the medial side of the joint between the bone 50 and bone 52 may increase. This may cause a spacer positioned within the joint to become unstable (e.g., because the spacer is no longer tightly engaged between the bones 50 and 52 due to the increased gap at the medial side of the joint).

Using the spacer 400 having the offset configuration within the joint during bone realignment can help stably maintain the spacer 400 within the joint. For example, because the spacer 400 can have the first portion 60 positioned in the joint closer to the lateral side than the medial side (e.g., at the lateral region of the joint such that the first sidewall 404 contacts the medial side of the second metatarsal 53) the spacer can be generally maintained at a constant position within the joint during this realignment. This can result because the spacing between the bones 50 and 52 at the lateral side of the joint during realignment may stay substantially constant or be reduced relative to the spacing before the realignment. As a result, the first portion 60 positioned at the lateral region can be stably held within the joint even after this realignment is completed. Furthermore, because the first portion 60 is stably maintained within the joint, the second portion 64, and central longitudinal axis 408 thereof, may also be generally maintained at its original position, such as at the center of the joint. This spacer 400 configuration, which may provide increased stability, can in turn be useful when the spacer 400 is utilized to facilitate preparation (e.g., cutting) of one or more bone surfaces, as will be described below with reference to FIG. 5.

Independent of whether a spacer is configured with a first portion aligned with a second portion (e.g., as discussed with respect to spacer 14) or a first portion offset relative to a second portion (e.g., as discussed with respect to spacer 400), the spacer can have a variety of different cross-sectional configurations. For example, while spacer 14 in FIGS. 1-3 and spacer 400 in FIGS. 4A and 4B are illustrated as having a constant thickness across the width of the spacer, the thickness of the spacer can vary over the width.

Figure 4C:
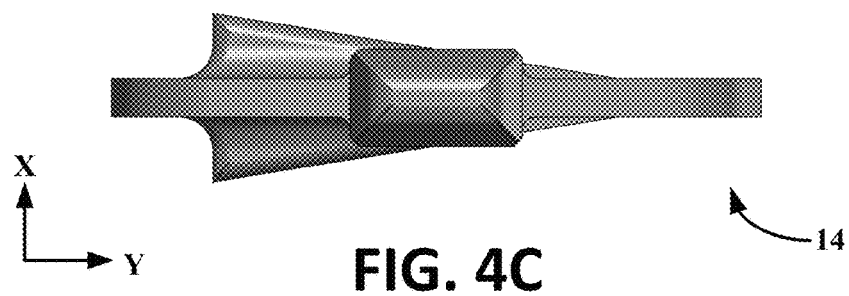
FIGS. 4C-4F illustrate an example configuration of a spacer where the thickness of the spacer varies across the width of the spacer.
Figures 4D, 4E, 4F:
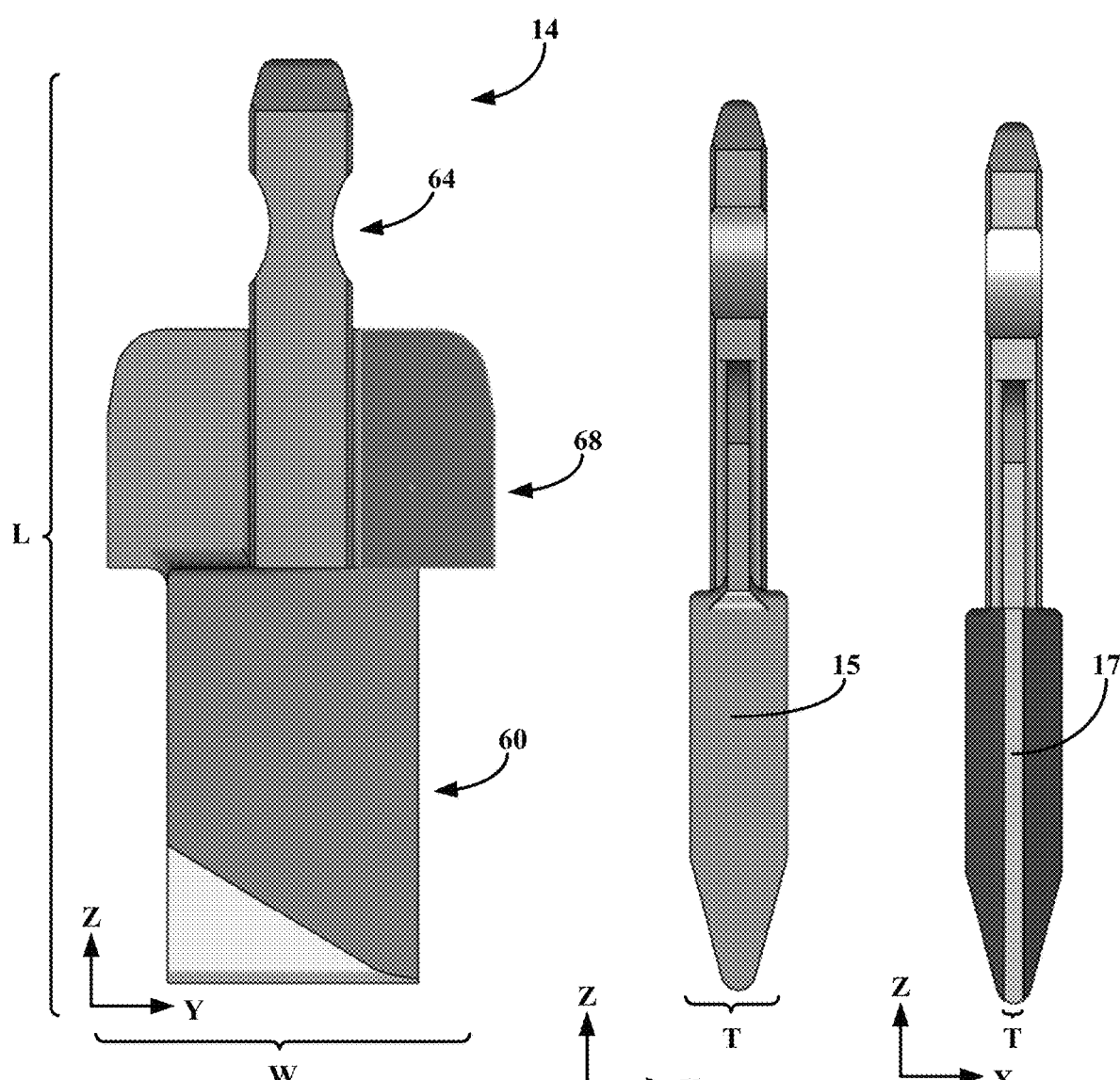

FIGS. 4C-4F illustrate an example configuration of spacer 14 where the thickness of the spacer varies across the width of the spacer. FIG. 4C is a top view of the example spacer; FIG. 4D is a front view of the spacer; and FIGS. 4E and 4F are opposite side views of the spacer. The Z-axis on the figures represents the vertical orientation of the spacer (e.g., dorsal to plantar direction) in typical use. As shown in the illustrated example, spacer 14 defines a length L (e.g., parallel to the longest axis of the spacer), a width W perpendicular to the length, and a thickness T perpendicular to both the length and width. The width W of the first portion 60 is the distance from the first sidewall 15 to the second sidewall 17 of the first portion. In the illustrated configuration, the thickness T of the spacer tapers across the width of the spacer from the first sidewall 15 to the second sidewall 17.

FIGS. 4G-4J similarly illustrates an example configuration of spacer 400 where the thickness of the spacer varies across the width of the spacer. FIG. 4G is a top view of the example spacer; FIG. 4H is a front view of the spacer; and FIGS. 4E and 4F are opposite side views of the spacer. Again, the Z-axis on the figures represents the vertical orientation of the spacer (e.g., dorsal to plantar direction) in typical use. As shown in the illustrated example, spacer 14 defines a length L (e.g., parallel to the longest axis of the spacer), a width W perpendicular to the length, and a thickness T perpendicular to both the length and width. The width W of the first portion 60 is the distance from the first sidewall 404 to the second sidewall 406 of the first portion. In the illustrated configuration, the thickness T of the spacer tapers across the width of the spacer from the first sidewall 404 to the second sidewall 406.

When configured with a differential thickness across its width, spacer 14 (FIGS. 4C-4F)/spacer 400 (FIGS. 4G-4J) is thicker on one side than the other side. In different examples, the spacer can have a continuous angle of taper across its width W or discontinuous taper, such one or more steps that define discrete thickness transition points. In some examples, the spacer has a thickness at least 0.1 mm less at its thinner sidewall compared to its thicker sidewall, such as at least 0.2 mm less, at least 0.5 mm less, or at least 1 mm less. For example, the spacer may have a thickness from 0.1 mm to 2 mm less at its thinner sidewall compared to its thicker sidewall. In addition, although second portion 64 and intermediate portion 68 of spacer 14/400 are illustrated as not being tapered, one or both of second portion 64 and intermediate portion 68 can be tapered in other embodiments.

In use, a spacer with tapered thickness may be positioned in a TMT joint with the thicker side of the spacer located medially and the thinner side of the spacer located laterally across the joint. During realignment of the first metatarsal relative to the medial cuneiform, a larger gap may open on the medial side between the end face of the first metatarsal and the end face of the medial cuneiform than on the lateral side. Accordingly, positioning the thicker portion of the spacer medially and the thinner portion of the spacer laterally across the TMT joint can help fill a gap between the bones, e.g., helping the spacer to fit snuggly within the TMT joint space and prevent inadvertent movement of the spacer.

Spacer 14/400 can have any suitable cross-section shape. For example, while spacer 14/400 is illustrated as defining a substantially rectangular shape, in other examples the spacer can define other shapes. Spacer 14/400 can define any polygonal (e.g., square, hexagonal) or arcuate (e.g., circular, elliptical) shape, or even combinations of polygonal and arcuate shapes. Indeed, first portion 60 of spacer 14/400 need not be a continuous structure across its width W but can be formed of discontinuous segments or portions of material which, in combination, achieve spacer functions.

Figure 4K:
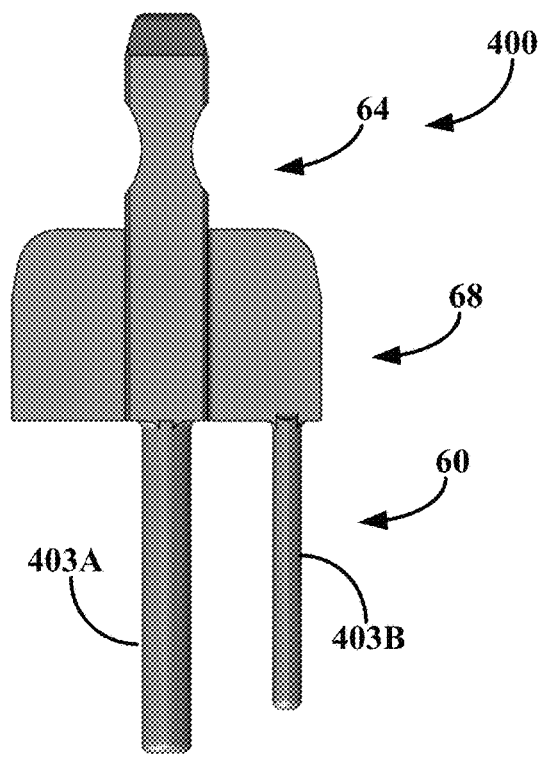
FIG. 4K illustrates an example configuration of a spacer that includes at least two pins separated from each other with a gap.

FIG. 4K illustrates an example configuration of spacer 400 where first portion 60 is formed by at least two pins 403A and 403B separated from each other with a gap therebetween. The pins 403A and 403B extend parallel to the length of the spacer (e.g., from intermediate portion 68 and/or second portion 64). In other configurations, spacer 400 may include more pins (e.g., three, four, or more) pins arrayed across at least a portion of the width of the spacer with a gap between each adjacent pin. Each pin can have the same cross-sectional dimension (e.g., diameter) or at least one pin can have a cross-sectional dimension greater than at least one other pin. For example, a medial-most pin (e.g., centered pin) may have a larger cross-sectional diameter than a lateral-most pin. Further, although pins 403A and 403B are illustrated as arranged to provide a laterally offset first portion 60, the pins may be arranged to provide a first portion that is centered with the second portion 64 or otherwise suitably arranged.

Figure 4L:
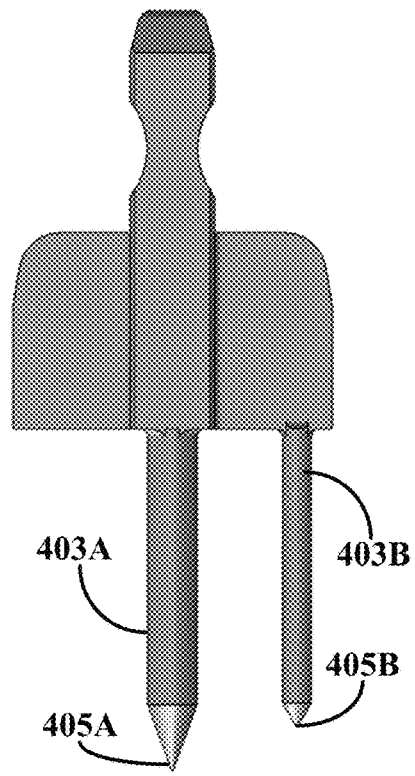
FIG. 4L illustrates an example configuration of the spacer in FIG. 4K where the ends of the pins are tapered to a point to facilitate insertion.
Figure 4M:
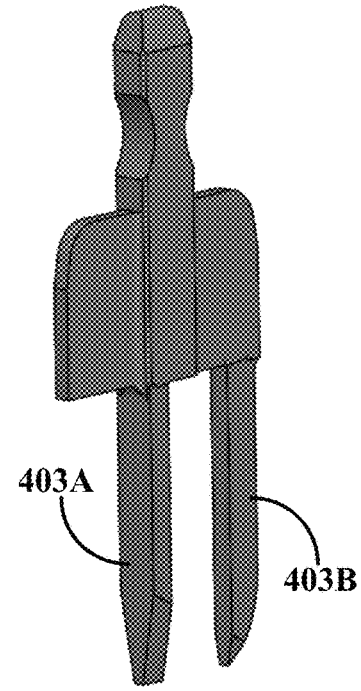
FIG. 4M illustrates an example configuration of the spacer in FIG. 4K where the pins have an alternative cross-sectional shape.

When configured with pins 403A and 403B, the ends or tips of the pins may be rounded and/or tapered (e.g., to a point) to provide for easier insertion of the pins into the space between two bones. FIG. 4L illustrates an example configuration of the spacer in FIG. 4K where the ends 405A and 405B of pins 403A and 403B, respectively, are tapered to a point to facilitate insertion. Further, pins 403A and 403B of spacer 400 can define any polygonal (e.g., square, hexagonal) or arcuate (e.g., circular, elliptical) shape, or even combinations of polygonal and arcuate shapes. For example, the pins can be cylindrical, trapezoidal, triangular, square, rectangular, oval, hexagonal, or have yet other cross-sectional shape. FIG. 4M illustrates an example configuration of the spacer in FIG. 4K where pins 403A and 403B have a rectangular cross-sectional shape (e.g., across the width of the pins).

Figure 5:
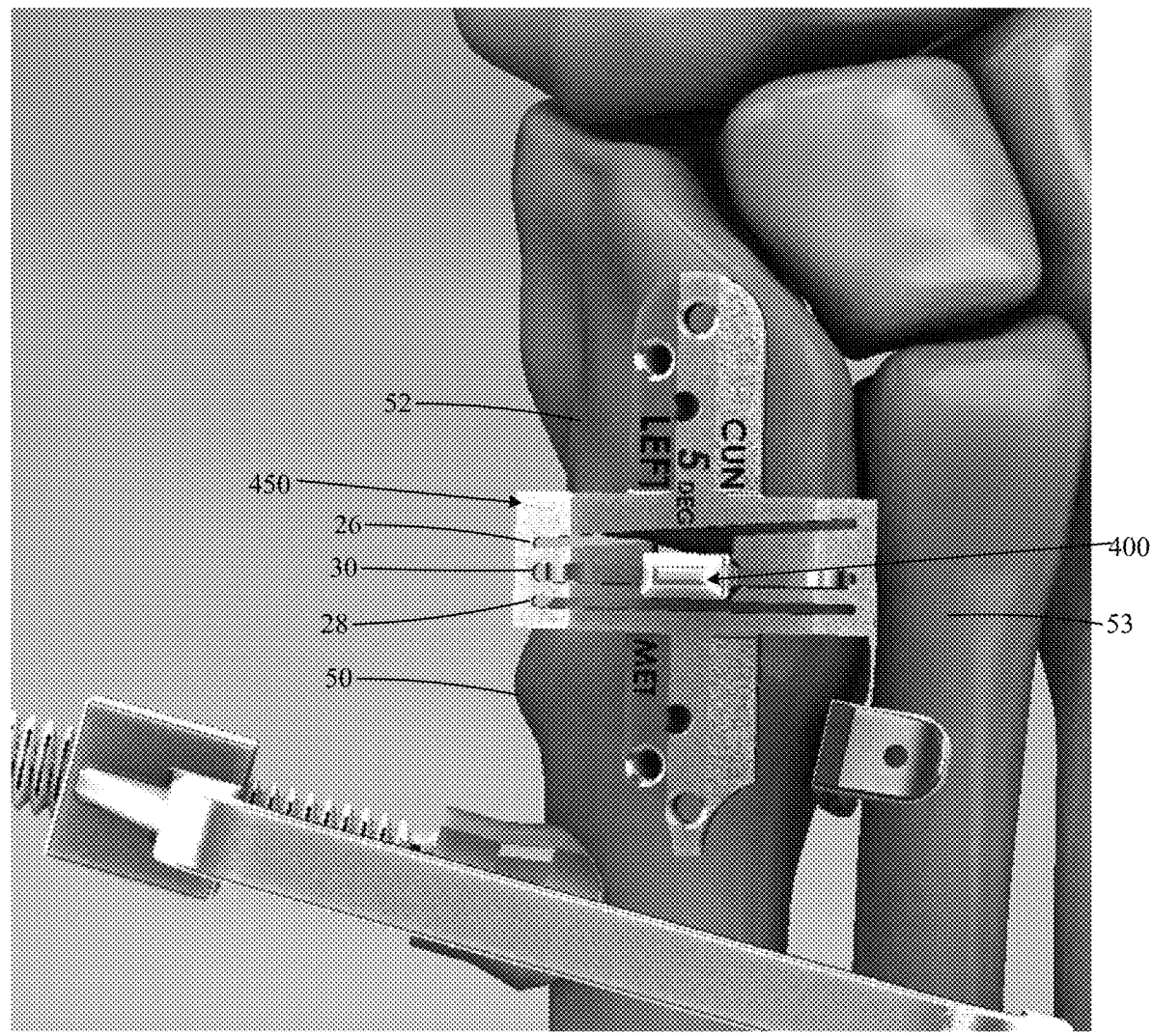
FIG. 5 is a top plan view of an embodiment of a bone preparing guide and the spacer of FIG. 4A on a foot in accordance with an embodiment of the invention.

FIG. 5 illustrates a top plan view of an embodiment of a bone preparing guide 450 and the spacer 400 on a foot. Like numerals used herein in connection with the bone preparing guide 450 refer to like elements of the bone preparing guide 12. As one example, the bone preparing guide 450 can be placed after one or more bones have been realigned by engaging the bone preparing guide 450 with the spacer 400 similar to that described previously. For instance, the bone preparing guide 450 can be engaged at the intermediate portion of the spacer 400 by moving the opening 30 of the guide 450 over the second portion of the spacer 400. As explained previously, using the spacer 400 can substantially maintain the intermediate and second portions, and thus central longitudinal axis thereof, at the desired position, such as at the center of the joint. Therefore, placing the guide 450 using the intermediate and/or second portions of the spacer 400 can result in alignment of the guide 450 at the desired position with respect to the joint, and thus bones 50 and 52. As a result, bone preparation can proceed efficiently using the guide 450.

While bone preparing guide 450 can have a variety of different configurations, as described above with respect to bone preparing guide 12, in the configuration illustrated in FIG. 5, bone preparing guide 450 includes a cutting slot 26 that is skewed form (e.g., oriented at an angle) relative to cutting slot 28 and/or the joint between bones 50 and 52. The slot 26 can be angled to an extent suitable for providing anatomically appropriate bone preparation (e.g., one or more bone cuts) depending on the procedure, and thus anatomical region, for which the guide 450 is used. Example angles of skew discussed above with respect to cut guide 12 can also be used for bone preparing guide 450.

Where the guide 450 is used to prepare one or more bones during a procedure on the foot as shown in the exemplary illustration of FIG. 5, the slot 26 can be angled relative to a TMT joint space and/or end of first metatarsal for cutting a portion of a cuneiform (e.g., medial cuneiform 52). The slot 26 can be angled proximally (e.g., away from the distal end of the medial cuneiform) as the slot extends from the medial side to the lateral side of the medial cuneiform. As a result, a cut made along slot 26 can result in a wedge being cut off the medial cuneiform that progressively increases in width (e.g., thickness) moving the medial side to the lateral side of the medial cuneiform.

In some examples, guide 450 is configured to be flipped in the frontal plane 180 degrees for interchangeable use on either the right or left foot of a patient. For example, if a TMT fusion procedure is being performed on the left foot of the patient, guide 450 may be rotated in a first orientation so slot 26 is angled proximal from the medial to lateral direction of the left foot. By contrast, if the TMT fusion procedure is being performed on the right foot of the patient, guide 450 may be rotated 180 degrees to a second orientation so slot 26 is angled proximal from the medial to lateral direction of the right foot. The top and bottom surfaces of guide 450 may be devoid of projections or other structural features that prevent the guide from being flipped and placed over a joint to be cut in order to configure the guide with skewed cutting slot for deployment on either foot.

In some examples, guide 450 with skewed slot 26 is provided as part of a kit that includes a plurality of different guides. The guides can vary by having different sizes and/or angles at which slot 26 is skewed relative to each other. During a procedure, a clinician can select one of the plurality of different guides, e.g., that best matches the size and/or angle of the cut desired to be made. To facilitate interchangeability of the guides during the procedure, each of the plurality of guides can have anchoring apertures (e.g., first and second adjustable stabilization members 46, 48) that are at the same location relative to each other (e.g., same separation distance and angle). When so configured, a clinician may remove one guide from anchoring pins set into first metatarsal 50 and medial cuneiform 52 (e.g., by pulling the guide up off the pins) and insert a different guide, for example having a slot 26 skewed at a different angle than the removed guide, over the same pins (e.g., by pushing the second guide down over the pins).

To help select an appropriate one of the plurality of available guides each having a cutting surface skewed at a different angle, a clinician may take an X-ray of a TMT joint being operated upon before selecting the guide. The clinician may take the X-ray from the dorsal to plantar direction to select and size the cut angle to be made on the medial cuneiform. The clinician may then select a particular one of the plurality of available guides whose angle best matches the size and/or angle of the cut to be made for subsequently deployment over the TMT joint, and particularly over the end of the medial cuneiform to be cut, during the procedure.

In the example of FIG. 5, the slot 26 is illustrated adjacent a cuneiform and thus can be configured at an angle proceeding proximally from the medial side to the lateral side of the guide 450, e.g., corresponding generally to bone preparation appropriate for a cuneiform (e.g., cutting a wedge-shaped portion of the cuneiform). That is, a cut made using slot 26 can produce a progressively thicker bone cut progressing from the medial to lateral side of the cuneiform bone. In some examples, an end of the slot 26 at the lateral side of the guide 450 can be angled between two and ten degrees relative to an end of the slot 26 at the medial side of the guide 450. In further examples, an end of the slot 26 at the lateral side of the guide 450 can be angled between two and five degrees relative to an end of the slot 26 at the medial side of the guide 450. Using the guide 450 having the angled slot 26 in conjunction with the spacer 400 as shown can provide for bone preparation of the bone 52 in an anatomically appropriate manner even after the bone 50 have been realigned.

Figure 6A:
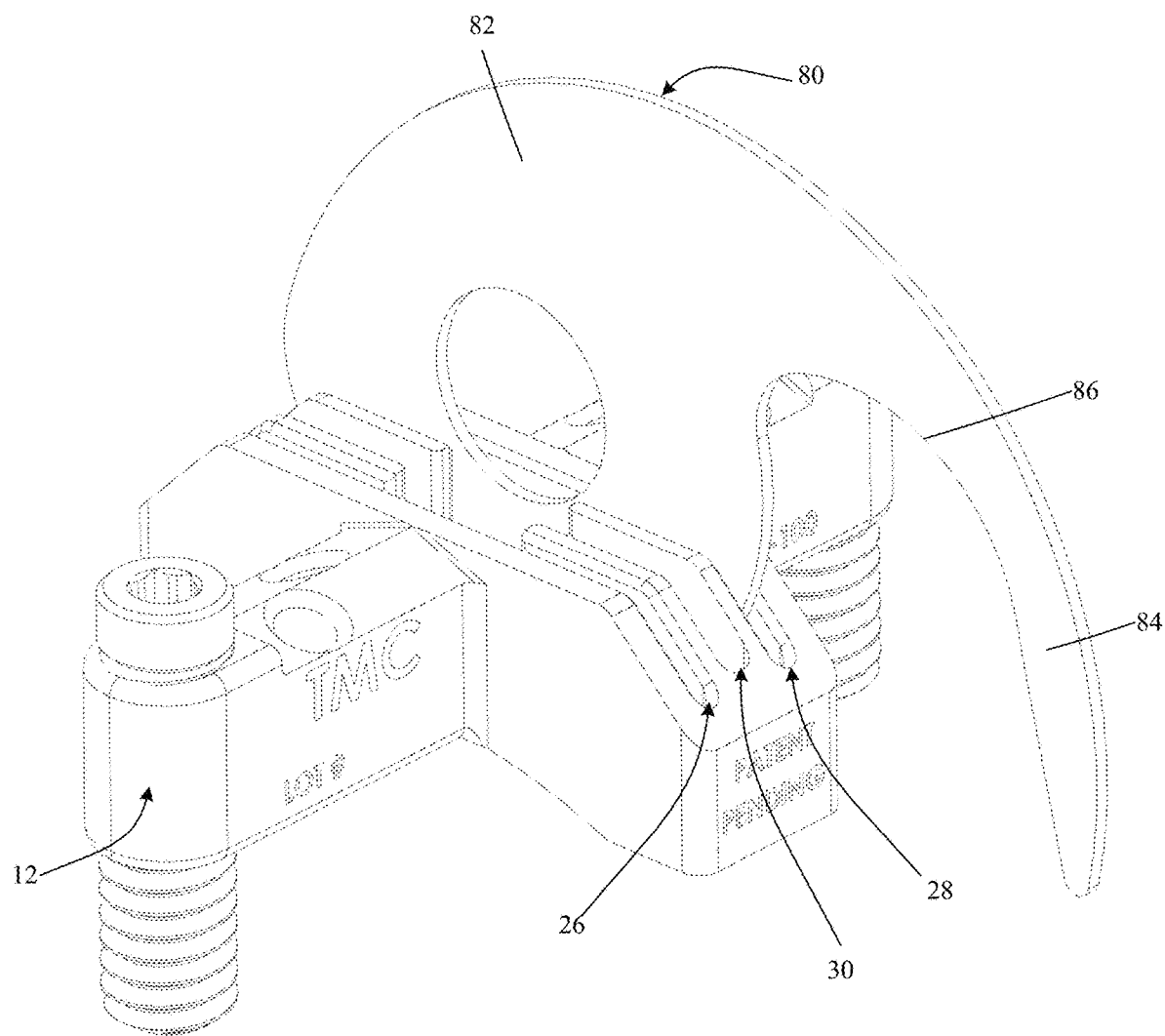
FIGS. 6A and 6B are perspective views of a bone preparing guide and a tissue removing instrument location check member in accordance with an embodiment of the invention.
Figure 6B:
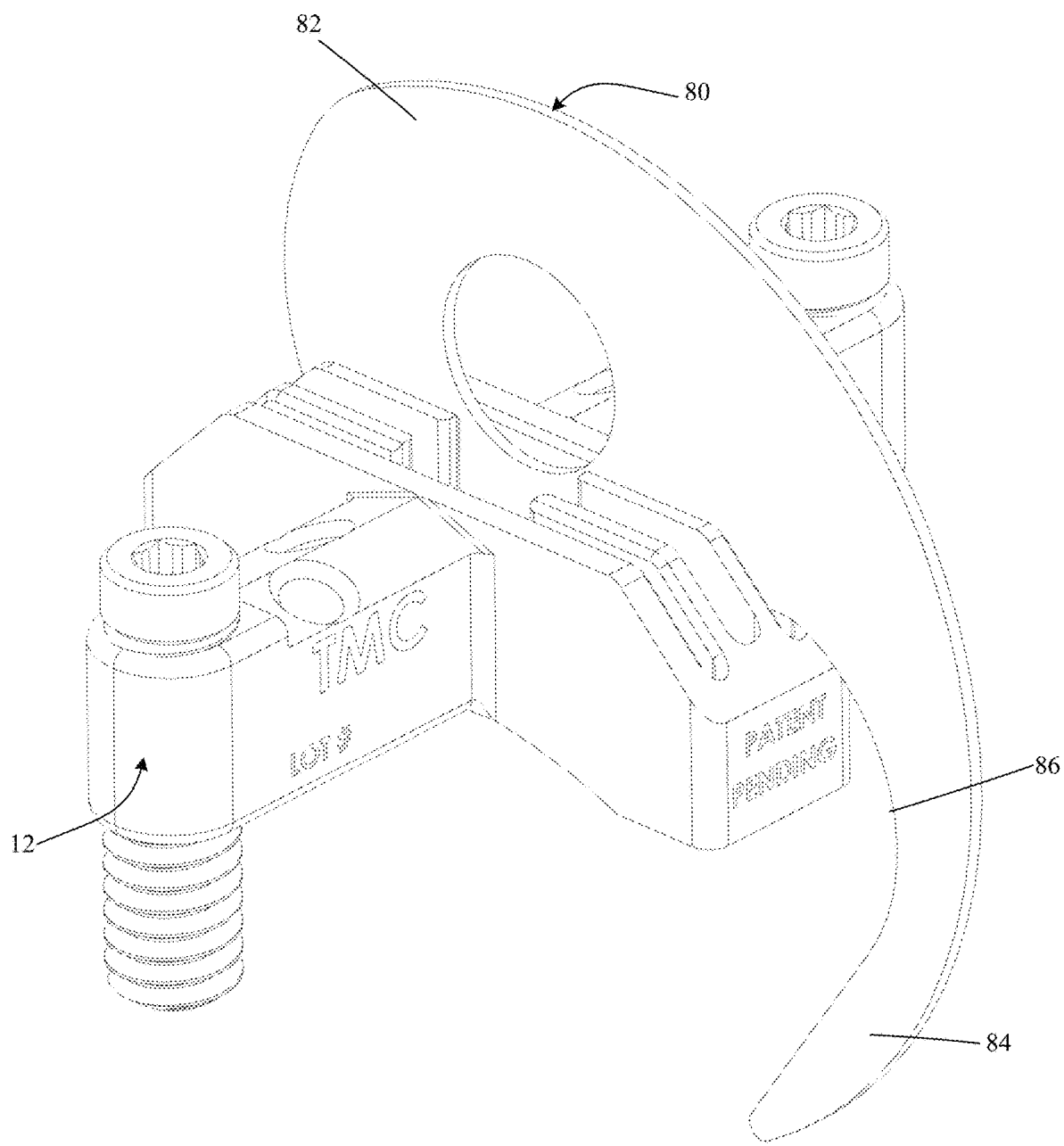
Figure 6C:
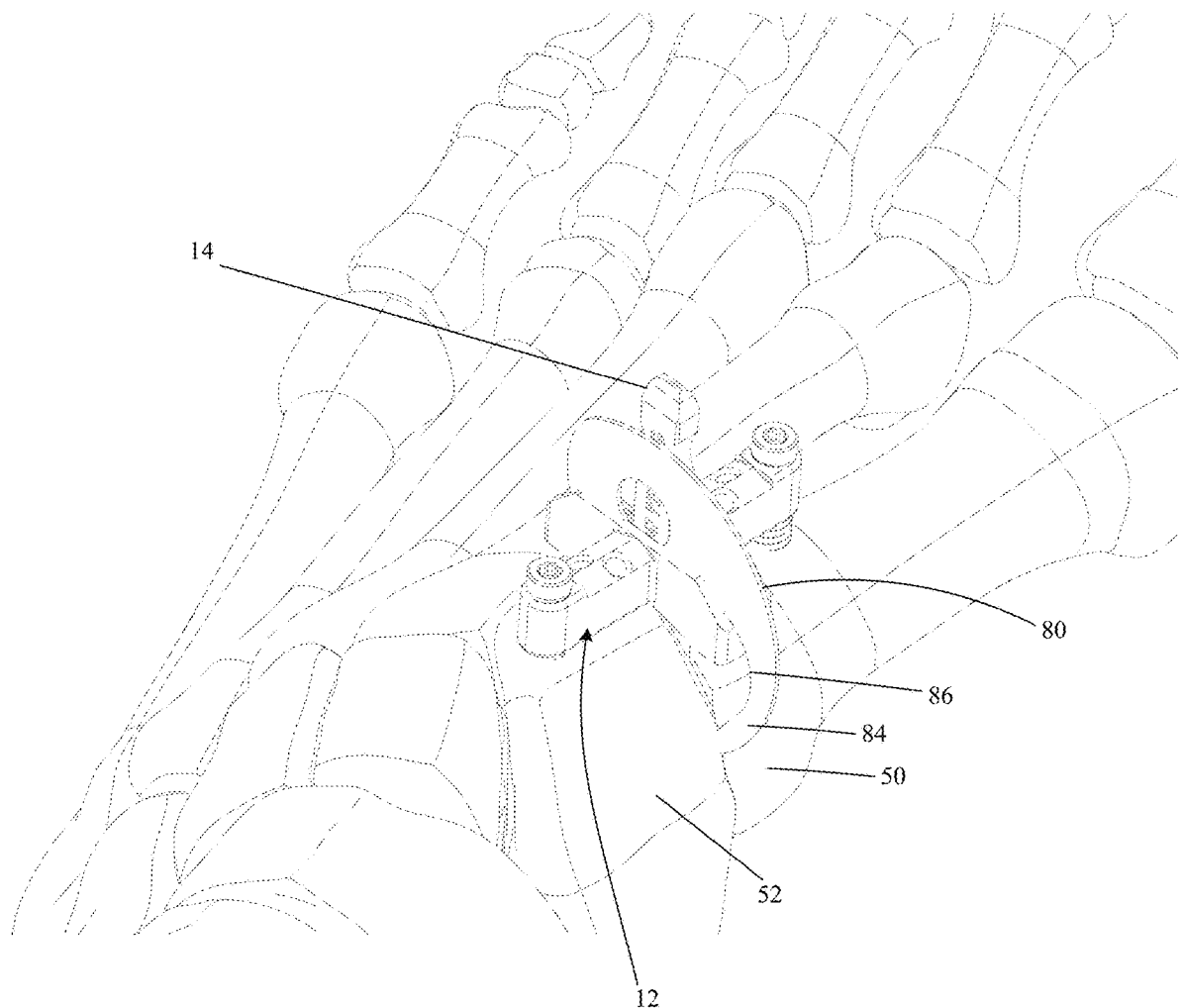
FIGS. 6C and 6D are perspective views of the bone preparing guide and tissue removing instrument location check member on a foot in accordance with an embodiment of the invention.
Figure 6D:
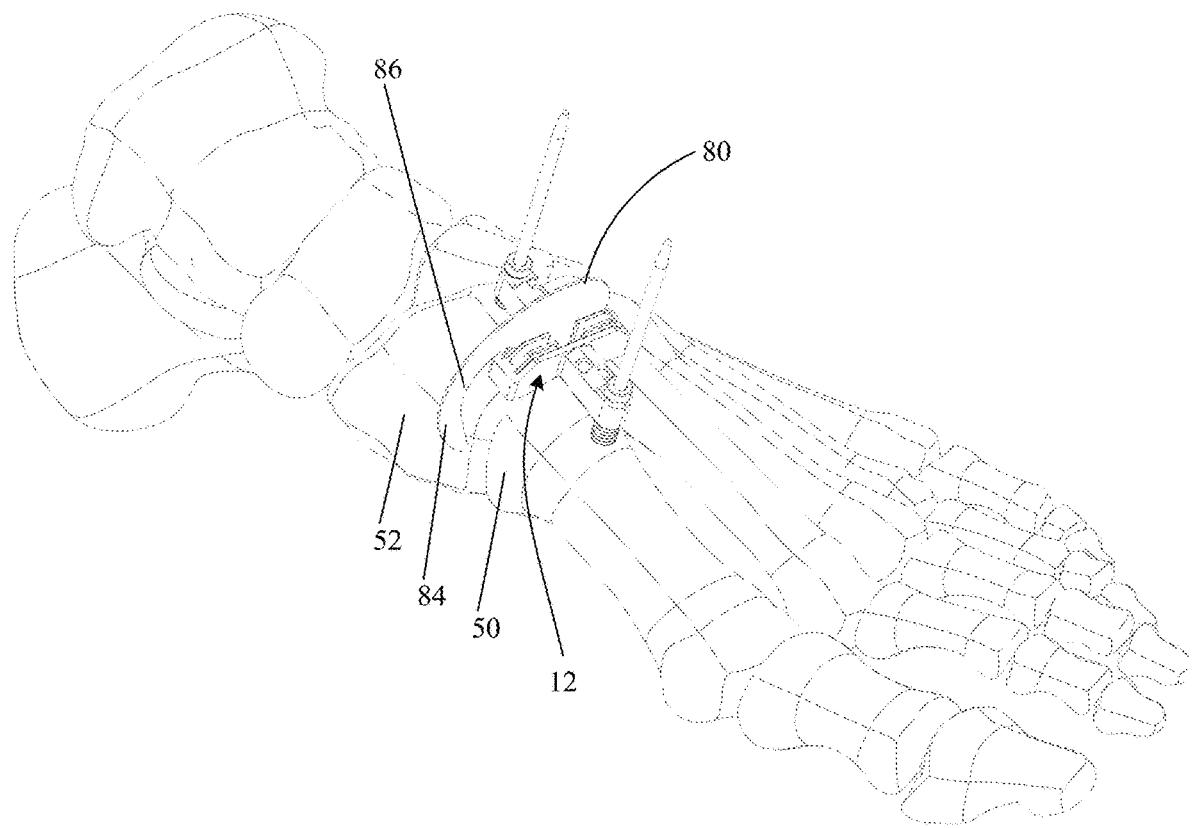

FIGS. 6A-6D show an embodiment of a tissue removal location check member 80. FIGS. 6A and 6B show perspective views of the bone preparing guide 12 and tissue removing instrument location check member 80 in isolation, while FIGS. 6C and 6D show perspective views of the bone preparing guide 12 and tissue removing instrument location check member 80 on a foot. The tissue removing instrument location check member 80 can serve to allow a surgeon to visualize the position and/or orientation of a cut to be made using the guide 12. In some embodiments, the spacer and tissue removing instrument location check member 80 can be engaged with the guide 12 at the same time.

The tissue removing instrument location check member 80 can include a first portion 82 and a second portion 84. In some embodiments, such as that shown, the member 80 may further include an opening 86 defined between the first portion 82 and the second portion 84. The member 80 can be engageable with the guide 12, such as at a slot 26 or 28 or opening 30, via the first portion 82 of the member 80. As shown, the first portion 82 is engaged with the guide 12 at the slot 28 and in some cases can extend down through the slot 28. In other examples, the first portion 82 can engage the guide 12 at the slot 26 or at the opening 30. Depending on the configuration of the tissue removing instrument location check member 80, the first portion 82 may in some instances engage the guide 12 at more than one of the slot 26, slot 28, and opening 30.

The second portion 84 is connected to or integral with the first portion 82 and extends and is spaced from the first portion 82. As illustrated, the second portion 84 can be configured to extend out from the guide 12 while the first portion 82 is engaged with the guide 12. For example, the first portion 82 can be within the slot 28 of the guide 12 while the second portion 84 is spaced from the first portion 82 in a direction (e.g., radial) outside of the slot 28. The second portion 84 can have a width less than a width of the first portion 82, and additionally may include curvature along its length. As shown, the second portion 84 includes curvature along its length in a direction toward the guide 12 when the first portion 82 is engaged with the guide 12. In embodiments where the opening 86 is included in the member 80, the opening 86 may be configured to receive a portion of a bone such that the second portion 84 can extend outwardly around such bone portion received in the opening 86.

The first portion 82 and the second portion 84 can be designed to be complimentary portions. In particular, in some examples, the position of the second portion 84 can in some predetermined manner correspond to the position of the first portion 82. For instance, where the member 80 is properly engaged with the guide 12, a tip of the second portion 84 can extend a same depth as a bottom edge of the first portion 82 (e.g., the tip of the second portion 84 and a bottom edge of the first portion 82 extend along a same plane). In such instance, visually inspecting a depth of the second portion 84 (e.g., extended outside of the guide 12) can provide an indication as to a depth of the first portion 82. This can be beneficial in applications where the bottom edge of the first portion 82 is inserted into tissue and not easily seen by a surgeon, but where the second portion 84 extends out from the tissue and can be seen by the surgeon. As such, in some examples the second portion 84 can allow a surgeon to ascertain how deep the first portion 82 is within the tissue by simply looking at the second portion 84 that is outside the tissue. In some cases, the depth of the second portion 84 can directly correspond to the depth of the first portion 82, and in other cases the correspondence between the first and second portions can be a predetermined ratio.

The tissue removing instrument location check member 80 can engage with the guide 12 in a manner that allows the member 80 to rotate relative to the guide 12 while engaged with the guide 12. This can be seen by comparing the position of the member 80 in FIG. 6A relative to the position of the member 80 in FIG. 6B. For example, the member 80 can be configured such that rotational movement applied to the member 80 may cause the second portion 84 to rotate about the guide 12 from the position shown in FIG. 6A to the position shown in FIG. 6B, which in some cases can result in the second portion 84 being positioned downward from the guide 12 while the first portion 82 is engaged in one of the slots 26, 28 or opening 30. The opening 86 can, in some applications, facilitate rotation of the second portion 84 about a portion of a bone by receiving a portion of such bone within the opening 86 and allowing the second portion 84 to extend outwardly around such bone. As such, the opening 86 can facilitate rotation of the member 80 while the member 80 is engaged with the guide 12 by preventing interference between the member 80 and a portion of a bone adjacent the second portion 84.

The member 80 can be engaged with the guide 12 when the guide 12 is placed onto a foot (as shown in FIGS. 6C and 6D). As described, the first and second portions 82, 84 can be designed as complimentary portions. In one such example, when the member 80 is engaged with the guide 12 on a foot, the first portion 82 can extend and contact a bone end at a same depth and location at which a cutting instrument would contact this bone end when using the guide 12 (e.g., via a slot defined in the guide). While the first portion 82 is extended to a bone, the second portion 84 of the member 80 can act as an external extension from the guide 12 that projects down the side of a bone (e.g., 50 or 52) at the same trajectory and/or depth that a cutting instrument would be positioned when inserted through a slot of the guide 12. This is because the first and second portions 82, 84 can be complimentary. Thus, the second portion 84 can act to provide an indication as to trajectory and/or depth at which a cutting instrument would contact a bone end. As such, the member 80 (e.g., the second portion 84 acting as an external extension) may allow a surgeon to check the position and/or orientation of one or more preparation slots of the guide 12 relative to one or more bone 50, 52 ends before performing the bone preparation action on the one or more bones 50, 52. Therefore, the member 80 can facilitate visualization of a cut depth and/or trajectory that would result from the current position and orientation of the guide 12 and allow a surgeon to adjust the position and/or orientation of the guide 12 as may be necessary for the desired application.

In some cases, in addition to or as an alternative to visualization using the member 80 (e.g. visualization of a position of complimentary second portion 84), imaging techniques (e.g., X-ray) can be used in conjunction with the member 80. For example, in one embodiment the member 80 can be engaged with the guide 12 such that the first portion 82 extends into tissue and contacts a bone end at a same depth and location at which a cutting instrument would contact this bone end when using the guide 12 in conjunction with the cutting instrument. The foot can then be imaged using an appropriate imaging technique while the first portion of the member 80 is within the tissue. Resulting images from the imaging technique can show the first portion of the member 80 relative to the bone end desired to be prepared in the specific application, and provide an indication as to a proposed cut depth and/or trajectory. In turn, this can allow a surgeon to adjust a position and/or orientation of the guide 12 as needed before performing the desired preparation action on this bone end.

The member 80 can be any component that projects from the guide (e.g., guide slot of a guide) in a manner that allows visualization of bone preparation position, trajectory, and/or thickness. In some cases, the spacer 14 and member 80 can both be used in a procedure to visualize proposed bone preparation and facilitate any adjustments to such bone preparation. As shown, the member 80 can be a separate component. As noted, the member 80 can engage with the guide 12, and in some examples can additionally or alternatively engage with the spacer 14. However, in other embodiments the member 80 can be integral with the spacer 14 and/or guide 12.

In some embodiments, the instrument location check member 80 is capable of showing where the tissue removing instrument will intersect both the first and second bones. Such an embodiment includes an instrument location check member with a first check member and a second check member (either or both of which can include some or all of the features described above with respect to a single member 80) connected together, such as with a bridge member. The first check member can be received within the guide slot 26 and the second check member can be received with the guide slot 28 at the same time.

Figure 7:
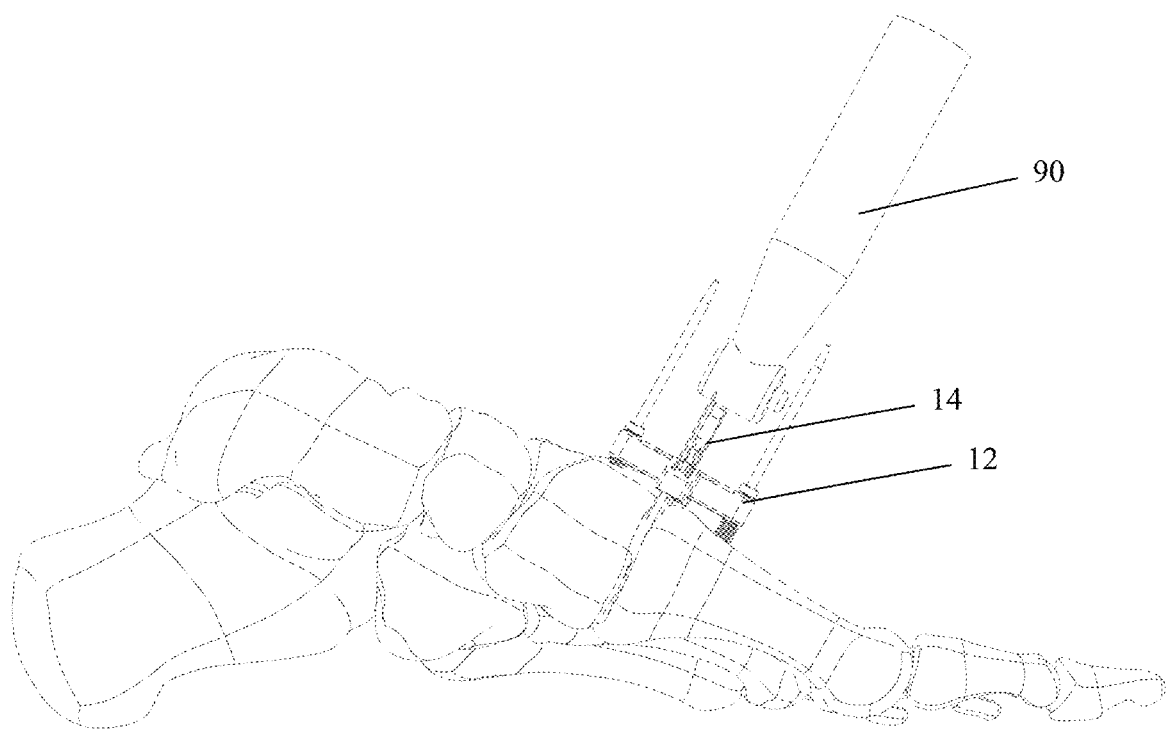
FIGS. 7 and 8 are perspective views of a tissue removing instrument used in conjunction with the bone preparing guide in accordance with an embodiment of the invention.
Figure 8:
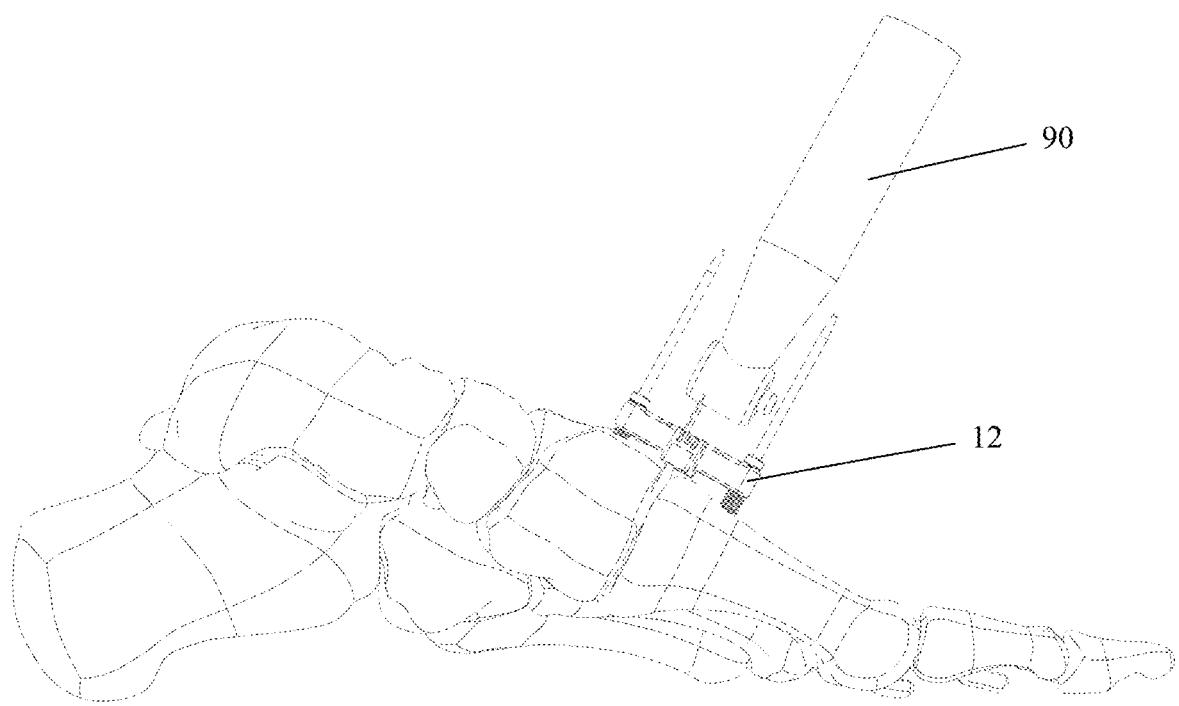

FIGS. 7 and 8 show perspective views of a tissue removing instrument 90 used in conjunction with the bone preparing guide 12. In some examples, such as in FIG. 7, the spacer 14 can be engaged with the guide 12 while the instrument 90 is used to prepare one or more bones. In other examples, such as in FIG. 8, the spacer 14 can be removed from the guide 12 prior to use of the instrument 90. Where the spacer 14 is removed, the guide 12 can be fixed in a position, such as by use of fixation devices through the guide 12, along the foot resulting from use of the spacer 14 as a reference.

Figure 9:
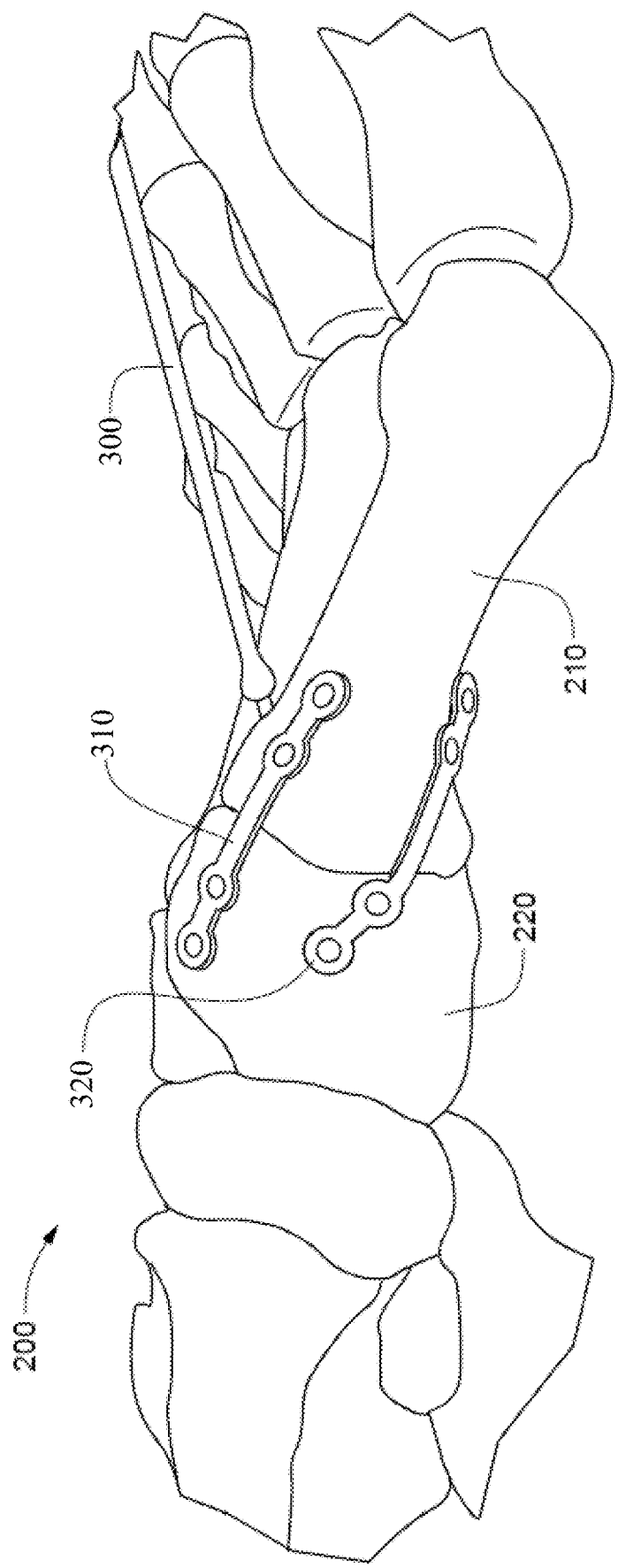
FIG. 9 is a side perspective view of a foot depicting bone plates across a joint between first and second bones in accordance with an embodiment of the invention.

FIG. 9 shows a side perspective view of a foot 200 depicting bone plates 310, 320 across a joint between a first metatarsal 210 and a medial cuneiform 220. After preparation of one or more bones, the ends of prepared bones can be placed in apposition, optionally compressed together, and fixed with a bone fixation device. FIG. 9 depicts a threaded olive pin 300 inserted through the first metatarsal 210 and into the medial cuneiform 220 to provide compression between the first metatarsal and the medial cuneiform. The position of the bones can then be fixed with one or more bone fixation devices. FIG. 9 shows a first bone plate 310 (e.g., a straight or curved bone plate positioned on a dorsal-medial side) and a second bone plate 320 (e.g., a helical bone plate positioned from a medial side of the cuneiform to a plantar side of the metatarsal (other embodiments, not shown, may include a second straight bone plate)) across the joint space. After the screws are inserted and/or the plates are applied with the insertion of bone screws, the olive pin may be removed.

Embodiments of the present invention also include methods, such as methods for fixing an orientation of a bone or bones. In general, one method of positioning a bone includes the steps of moving a bone from an anatomically misaligned position to an anatomically aligned position with respect to another bone and, after moving the bone into the aligned position, preparing an end of the moved bone and a facing end of another bone.

In some embodiments, a method includes the step of preparing a joint for a corrective procedure. For example, after creating surgical access to the joint and before moving the bones into an aligned position, soft tissue can be released to allow a bone, such as a metatarsal, to rotate freely. In some embodiments, obstructing bone may be excised (e.g., a flare of the metatarsal base, or osteophyte) to further promote free rotation.

In some embodiments, the location of the intersection of the tissue removing instrument and the bone to be prepared is confirmed before bone preparation. In one embodiment, a tissue removing instrument location check member can be engaged with the preparation guide to visually confirm where a tissue removal instrument will contact the bone. In another embodiment, a tissue spacer is engaged with the preparation guide to provide a reference for a position and/or orientation of a cut made through one or more defined by the guide. In either embodiment, such visual confirmation can include the use of an imaging device, such as an X-ray. If the position of the preparation guide is correct, additional fixation devices (e.g., pins) may be inserted through the apertures (e.g., angled apertures) to further fix the position of the preparation guide with respect to the first metatarsal and the medial cuneiform, or other bones depending on the application. In embodiments where the spacer and guide are provided as separate components, the spacer can be reattached prior to further bone preparation steps.

After proper alignment of the bones and the preparation guide, the end of a first metatarsal facing the medial cuneiform, for instance, can be prepared with a tissue removing instrument aligned with the first guide surface, such as by inserting the tissue removing instrument through a slot defined by the first guide surface and a first facing surface. And the end of the medial cuneiform facing the first metatarsal can be prepared with the tissue removing instrument aligned with a second guide surface, such as by inserting the tissue removing instrument through a slot defined by the second guide surface and a second facing surface. In embodiments that include cutting bone or cartilage, the cuneiform cut and the metatarsal cut can be parallel, conforming cuts. After the bones are prepared the guide and any other bone preparation members can be removed and the tissue (e.g., bone or cartilage slices) can be removed from the joint site.

As noted, embodiments of methods in accordance with the invention can also include steps performed after preparing the ends of the bones. For example, the ends of the bones may be placed in apposition and optionally compressed together and the position of the bones can be fixed with one or more bone fixation devices (e.g., compressing bone screw, bone plate, bone staple, external fixator, intramedullary implant or nail) prior to a closing of the surgical access to the joint.

For instance, in view of the details provided herein, one method can include inserting a spacer into a joint (e.g., TMT joint space) and then engaging the guide with the inserted spacer (in embodiments where the guide and the spacer are provided as separate components). Alternatively, the spacer can be inserted into the joint while the guide is placed onto the foot (in embodiments where the guide and the spacer are provided as separate components). In another embodiment, the guide and the spacer can be positioned together. Then, the spacer can be used as a reference for positioning and/or orienting the guide at an appropriate location relative to one or more bones for an intended application. In some examples, a tissue removing instrument location check member can additionally or alternatively be used to provide an indication as to a depth and/or trajectory of a cut to be made through a slot defined by the guide on the foot. In some cases, the location of the guide relative to the one or more bones to be prepared may be adjusted according to references obtained from the spacer and/or tissue removing instrument location check member. After the guide is appropriately located, the guide can be fixed to the foot, such as through fixation devices (e.g., pins) inserted through apertures defined in the guide. After fixing the guide to the foot, the spacer and/or tissue removing instrument location check member may be removed. In some examples, the spacer and/or tissue removing instrument location check member can remain engaged with the guide after the guide is fixed to the foot so long as no interference with the tissue removing instrument will result. A tissue removing instrument can then be inserted through the guide (e.g., through a slot defined in the guide) to prepare one or more bones at the location of the fixed guide. Any cut portions of bone resulting from use of the tissue removing instrument can be removed from the joint. The prepared bones can have their respective ends apposed together and fixation (e.g., one or more bone plates) can be applied for fusion of the prepared bone ends.

Embodiments of the invention also include a disposable, sterile kit that includes an embodiment of a bone positioning guide, bone preparation guide, spacer, and/or tissue removing instrument location check member described herein. Other components that may be included within the sterile kit include bone fixation devices, such as bone plates and/or pins, and tissue removing instruments.

Thus, embodiments of the invention are disclosed. Although the present invention has been described with reference to certain disclosed embodiments, the disclosed embodiments are presented for purposes of illustration, and not limitation, and other embodiments of the invention are possible. One skilled in the art will appreciate that various changes, adaptations, and modifications may be made without departing from the spirit of the invention.

The invention claimed is:

1. A method of preparing a tarsometatarsal joint, the method comprising:
   imaging a tarsometatarsal joint of a patient between a metatarsal and a cuneiform to determine a size and/or angle of a wedge-shaped bone portion to be cut at the tarsometatarsal joint;
   obtaining a bone preparation guide comprising a first guide surface positionable over the metatarsal and a second guide surface positionable over the cuneiform, wherein an angle of the first guide surface relative to the second guide surface is selected corresponding to the size and/or angle of the wedge-shaped bone portion to be cut as determined via imaging of the tarsometatarsal joint;
   positioning the first guide surface of the bone preparation guide over the metatarsal and positioning the second guide surface of the bone preparation guide over the cuneiform;
   guiding a tissue removing instrument with the first guide surface to cut an end of the metatarsal; and
   guiding the tissue removing instrument with the second guide surface to cut an end of the cuneiform.

2. The method of claim 1, wherein positioning the first guide surface of the bone preparation guide over the metatarsal and positioning the second guide surface of the bone preparation guide over the cuneiform comprises:
   positioning the first guide surface parallel to the end of the metatarsal and positioning the second guide surface at an angle relative to the end of the cuneiform to remove the wedge-shaped bone portion from the cuneiform;
   positioning the first guide surface at an angle relative to the end of the metatarsal to remove the wedge-shaped bone portion from the metatarsal and positioning the second guide surface parallel to the end of the cuneiform; or
   positioning the first guide surface at the angle relative to the end of the metatarsal to remove one wedge-shaped bone portion from the metatarsal and positioning the second guide surface at the angle relative to the end of the cuneiform to remove another wedge-shaped bone portion from the cuneiform.

3. The method of claim 1, wherein the wedge-shaped bone portion is a plantar-based wedge.

4. The method of claim 1, wherein the first guide surface is angled relative to the second guide surface at an angle within a range from 2 degrees to 10 degrees.

5. The method of claim 1, wherein imaging the tarsometatarsal joint of the patient comprises obtaining an X-ray of the tarsometatarsal joint.

6. The method of claim 1, further comprising inserting a check member into the bone preparation guide and using the check member to check the position and/or orientation of the bone preparation guide relative to the metatarsal and/or cuneiform prior to guiding the tissue removing instrument with the first guide surface to cut the end of the metatarsal and prior to guiding the tissue removing instrument with the second guide surface to cut the end of the cuneiform.

7. The method of claim 1, wherein:
   the bone preparation guide further comprises a spacer extending from the bone preparation guide; and
   positioning the first guide surface of the bone preparation guide over the metatarsal and positioning the second guide surface of the bone preparation guide over the cuneiform comprises inserting the spacer into the tarsometatarsal joint.

8. The method of claim 7, wherein the spacer is integral with the bone preparation guide such that the bone preparation guide and spacer are a single component.

9. The method of claim 7, wherein positioning the first guide surface of the bone preparation guide over the metatarsal and positioning the second guide surface of the bone preparation guide over the cuneiform comprises positioning the bone preparation guide at a target position along a length of the metatarsal and cuneiform and at a target orientation relative to the metatarsal and cuneiform in one or more planes.

10. The method of claim 1, wherein a distance between the first guide surface and the second guide surface is within a range from 2 mm to 10 mm.

11. The method of claim 1, wherein the bone preparation guide extends from a first end to a second end, the first end comprises at least one fixation aperture, and the second end comprises at least one fixation aperture, and further comprising:
   positioning the first end of the bone preparation guide over the metatarsal and inserting a fixation pin through the at least one fixation aperture of the first end to secure the bone preparation guide to the metatarsal; and
   positioning the second end of the bone preparation guide over the cuneiform and inserting a fixation pin through the cuneiform to secure the bone preparation guide to the cuneiform.

12. The method of claim 11, wherein at least one fixation aperture of the first end is skewed relative to at least one fixation aperture of the second end.

13. The method of claim 1, wherein the bone preparation guide comprises:
   a first facing surface positioned adjacent to the first guide surface to define a first slot therebetween; and
   a second facing surface positioned adjacent to the second guide surface to define a second slot therebetween.

14. The method of claim 13, wherein one of the first facing surface and the second facing surface contains a gap along its length.

15. The method of claim 1, wherein the bone preparation guide having the angle of the first guide surface relative to the second guide surface selected corresponding to the size and/or angle of the wedge-shaped bone portion to be cut as determined via imaging of the tarsometatarsal joint is designated by an identification number.

16. The method of claim 1, further comprising moving the metatarsal relative to the cuneiform in multiple planes.

17. The method of claim 16, further comprising, prior to moving the metatarsal, performing a soft tissue release to allow the metatarsal to rotate.

18. The method of claim 17, wherein guiding the tissue removing instrument with the first guide surface to cut the end of the metatarsal and guiding the tissue removing instrument with the second guide surface to cut the end of the cuneiform comprises guiding the tissue removing instrument with the first guide surface to cut the end of the metatarsal and guiding the tissue removing instrument with the second guide surface to cut the end of the cuneiform before moving the metatarsal relative the cuneiform in multiple planes.

19. The method of claim 1, further comprising, after preparing the end of the metatarsal and the end of the cuneiform:
compressing a prepared end of the metatarsal and a prepared end of the cuneiform together; and
fixing a position of the metatarsal relative to the cuneiform using one or more bone fixation devices.

20. The method of claim 1, wherein guiding the tissue removing instrument with the first guide surface to cut the end of the metatarsal comprises guiding the tissue removing instrument with the first guide surface to cut the end of the metatarsal after guiding the tissue removing instrument with the second guide surface to cut the end of the cuneiform.

21. A method of preparing a tarsometatarsal joint, the method comprising:
imaging a tarsometatarsal joint of a patient between a metatarsal and a cuneiform to determine a size and/or angle of a wedge-shaped bone portion to be cut from the cuneiform;
obtaining a bone preparation guide comprising a first guide surface positionable over the metatarsal and a second guide surface positionable over the cuneiform, wherein an orientation of the first guide surface relative to the second guide surface is selected corresponding to the size and/or angle of the wedge-shaped bone portion to be cut from the cuneiform as determined via imaging of the tarsometatarsal joint;
positioning the first guide surface of the bone preparation guide over the metatarsal and positioning the second guide surface of the bone preparation guide over the cuneiform;
guiding a tissue removing instrument with the first guide surface to cut an end of the metatarsal;
guiding the tissue removing instrument with the second guide surface to cut the wedge-shaped bone portion from an end of the cuneiform;
moving the metatarsal relative to the cuneiform in multiple planes;
compressing a prepared end of the metatarsal and a prepared end of the cuneiform together; and
fixing a position of the metatarsal relative to the cuneiform using one or more bone fixation devices.

22. The method of claim 21, wherein positioning the first guide surface of the bone preparation guide over the metatarsal and positioning the second guide surface of the bone preparation guide over the cuneiform comprises positioning the first guide surface parallel to the end of the metatarsal and positioning the second guide surface at an angle relative to the end of the cuneiform to remove the wedge-shaped bone portion from the cuneiform.

23. The method of claim 21, wherein imaging the tarsometatarsal joint of the patient comprises obtaining an X-ray of the tarsometatarsal joint.

24. The method of claim 21, wherein:
the bone preparation guide further comprises a spacer extending from the bone preparation guide, wherein the spacer is integral with the bone preparation guide such that the bone preparation guide and spacer are a single component; and
positioning the first guide surface of the bone preparation guide over the metatarsal and positioning the second guide surface of the bone preparation guide over the cuneiform comprises inserting the spacer into the tarsometatarsal joint.

25. The method of claim 21, wherein the bone preparation guide extends from a first end to a second end, the first end comprises at least one fixation aperture, and the second end comprises at least one fixation aperture, and further comprising:
positioning the first end of the bone preparation guide over the metatarsal and inserting a fixation pin through the at least one fixation aperture of the first end to secure the bone preparation guide to the metatarsal; and
positioning the second end of the bone preparation guide over the cuneiform and inserting a fixation pin through the cuneiform to secure the bone preparation guide to the cuneiform.

26. The method of claim 21, wherein guiding the tissue removing instrument with the first guide surface to cut the end of the metatarsal and guiding the tissue removing instrument with the second guide surface to cut the end of the cuneiform comprises guiding the tissue removing instrument with the first guide surface to cut the end of the metatarsal and guiding the tissue removing instrument with the second guide surface to cut the end of the cuneiform before moving the metatarsal relative the cuneiform in multiple planes.

27. A method of preparing a tarsometatarsal joint, the method comprising:
imaging a tarsometatarsal joint of a patient between a metatarsal and a cuneiform to determine a size and/or angle of a wedge-shaped bone portion to be cut at the tarsometatarsal joint;
obtaining a bone preparation guide comprising a first guide surface positionable over the metatarsal and a second guide surface positionable over the cuneiform, wherein an angle of the first guide surface relative to the second guide surface is selected corresponding to the size and/or angle of the wedge-shaped bone portion to be cut as determined via imaging of the tarsometatarsal joint;
positioning the first guide surface of the bone preparation guide over the metatarsal and positioning the second guide surface of the bone preparation guide over the cuneiform;
guiding a tissue removing instrument with the first guide surface to cut an end of the metatarsal;
guiding the tissue removing instrument with the second guide surface to cut an end of the cuneiform; and
moving the metatarsal relative to the cuneiform using a bone positioner.

28. The method of claim 27, further comprising, after preparing the end of the metatarsal and the end of the cuneiform:

compressing a prepared end of the metatarsal and a prepared end of the cuneiform together; and fixing a position of the metatarsal relative to the cuneiform using one or more bone fixation devices.

29. The method of claim 27, wherein positioning the first guide surface of the bone preparation guide over the metatarsal and positioning the second guide surface of the bone preparation guide over the cuneiform comprises positioning the first guide surface parallel to the end of the metatarsal and positioning the second guide surface at an angle relative to the end of the cuneiform to remove the wedge-shaped bone portion from the cuneiform.

30. The method of claim 27, wherein moving the metatarsal relative to the cuneiform comprises moving the metatarsal relative to cuneiform in one or more of a frontal plane, a transverse plane, and a sagittal plane.

* * * * *